United States Patent
Park et al.

(10) Patent No.: US 7,833,635 B2
(45) Date of Patent: Nov. 16, 2010

(54) ORGANOELECTROLUMINESCENT COMPOUND AND ORGANOELECTROLUMINESCENT DEVICE EMPLOYING THE SAME

(75) Inventors: Sang-Hoon Park, Yongin-si (KR); Yu-Jin Kim, Yongin-si (KR); O-Hyun Kwon, Yongin-si (KR); Byoung-Ki Choi, Yongin-si (KR); Jhun-Mo Son, Yongin-si (KR)

(73) Assignee: Samsung Mobile Display Co., Ltd., Giheung-Gu, Yongin, Gyunggi-Do (KR)

( * ) Notice: Subject to any disclaimer, the term of this patent is extended or adjusted under 35 U.S.C. 154(b) by 574 days.

(21) Appl. No.: 11/826,808

(22) Filed: Jul. 18, 2007

(65) Prior Publication Data

US 2008/0093987 A1      Apr. 24, 2008

(30) Foreign Application Priority Data

Oct. 23, 2006   (KR) .................... 10-2006-0103144

(51) Int. Cl.
*H01J 1/61* (2006.01)
(52) U.S. Cl. .................. 428/690; 313/504; 544/102; 544/35
(58) Field of Classification Search ................ None
See application file for complete search history.

(56) References Cited

U.S. PATENT DOCUMENTS

| | | | |
|---|---|---|---|
| 4,356,429 A | 10/1982 | Tang | |
| 4,885,211 A | 12/1989 | Tang et al. | |
| 5,151,629 A | 9/1992 | VanSlyke | |
| 2005/0074630 A1* | 4/2005 | Kanno et al. | ............... 428/690 |
| 2005/0106418 A1* | 5/2005 | Kim et al. | ................... 428/690 |
| 2008/0079356 A1 | 4/2008 | Park et al. | |
| 2008/0100207 A1 | 5/2008 | Park et al. | |

FOREIGN PATENT DOCUMENTS

JP     11-003782     4/1999

OTHER PUBLICATIONS

Baba et. al., Investigating Work Function Tunable Hole-Injection-Transport Layers . . . , J. Phys. Chem., 2004, 108, p. 18949-18955.*
Yoshiyuki Kuwabara et al., "Thermally Stable Multilayered Organic Electrolunimescent Devices Using Novel Starburst Molecules, 4,4',4"-Tri(N-carbazolyl)triphenylamine (TCTA) and 4,4',4"-Tris(3-methylphenylphenyl-amino)triphenylamine(m-MTDATA),asHole-Transport Materials", Adv. Mater. 1994, 6, No. 9, pp. 677-679.

* cited by examiner

*Primary Examiner*—D. Lawrence Tarazano
*Assistant Examiner*—Gregory Clark
(74) *Attorney, Agent, or Firm*—Robert E. Bushnell, Esq.

(57) ABSTRACT

A cyclopentaphenanthrene-based compound is easy to prepare and excellent in solubility, color purity, color stability, and thermal stability. The cyclopentaphenanthrene-based compound is useful as a material for forming an organic layer, in particular, an emitting layer, in an organoelectroluminescent device, and as an organic dye or an electronic material such as a nonlinear optical material.

20 Claims, 4 Drawing Sheets

ORGANOELECTROLUMINESCENT COMPOUND AND ORGANOELECTROLUMINESCENT DEVICE EMPLOYING THE SAME

CROSS-REFERENCE TO RELATED PATENT APPLICATION AND CLAIM OF PRIORITY

This application claims priority from Korean Patent Application No. 10-2006-0103144, filed on Oct. 23, 2006, in the Korean Intellectual Property Office, the disclosure of which is incorporated herein in its entirety by reference.

BACKGROUND OF THE INVENTION

1. Field of the Invention

The present invention relates to a cyclopentaphenanthrene-based compound and an organoelectroluminescent device employing the same. More particularly, the present invention relates to a cyclopentaphenanthrene-based compound and an organoelectroluminescent device including an organic layer formed of the cyclopentaphenanthrene-based compound.

2. Description of the Related Art

Organoelectroluminescent devices are active emission display devices that emit light by recombination of electrons and holes in a thin layer (hereinafter, referred to as "organic layer") formed of a fluorescent or phosphorescent organic compound when a current is supplied to the organic layer. The organoelectroluminescent devices have advantages such as lightness, simple constitutional elements, an easy fabrication process, superior image quality, and a wide viewing angle. In addition, the organoelectroluminescent devices can perfectly create dynamic images, achieve high color purity, and have electrical properties suitable for portable electronic equipment due to low power consumption and low driving voltage.

Eastman Kodak Co. has developed an organoelectroluminescent device with a multi-layered structure including an aluminum quinolinol complex layer and a triphenylamine derivative layer (U.S. Pat. No. 4,885,211), and an organoelectroluminescent device including an organic light-emitting layer formed of a low molecular weight material capable of emitting light in a broad wavelength range from UV to infrared light (U.S. Pat. No. 5,151,629).

Light-emitting devices are self-emitting devices and have advantages such as a wide viewing angle, good contrast, and a rapid response time. Light-emitting devices can be classified into inorganic light-emitting devices using an emitting layer formed of an inorganic compound and organic light-emitting devices (OLEDs) using an emitting layer formed of an organic compound. OLEDs show better brightness, driving voltage, and response speed characteristics and can create polychromatic light, compared to inorganic light-emitting devices, and thus, extensive research into OLEDs has been conducted.

Generally, OLEDs have a stacked structure including an anode, an organic light-emitting layer, and a cathode. OLEDs may also have various structures such as anode/hole injection layer/hole transport layer/emitting layer/electron transport layer/electron injection layer/cathode or anode/hole injection layer/hole transport layer/emitting layer/hole blocking layer/electron transport layer/electron injection layer/cathode.

Materials used for OLEDs can be classified into vacuum-depositable materials and solution-coatable materials according to an organic layer formation process. Vacuum-depositable materials must have a vapor pressure of $10^{-6}$ torr or more at 500° C. or less, and may be low molecular weight materials having a molecular weight of 1,200 or less. Solution-coatable materials must have solubility sufficient to form solutions, and include mainly an aromatic or heterocyclic ring.

When manufacturing organoelectroluminescent devices using a vacuum deposition process, manufacturing costs may increase due to use of a vacuum system, and it may be difficult to manufacture high-resolution pixels for natural color displays using a shadow mask. On the other hand, when manufacturing organoelectroluminescent devices using a solution coating process, e.g., inkjet printing, screen printing, or spin coating, the manufacturing process is simple, manufacturing costs are low, and a relatively high resolution can be achieved compared to when using a shadow mask.

However, when using solution-coatable materials, the performance (e.g., thermal stability, color purity) of light-emitting molecules is lowered compared to when using vacuum-depositable materials. Even though the light-emitting molecules of the solution-coatable materials have good performance, there arise problems that the materials, when formed into an organic layer, are gradually crystallized to grow into a size corresponding to a visible light wavelength range, and thus, the grown crystals scatter visible light, thereby causing a turbidity phenomenon, and pinholes, etc. may be formed in the organic layer, thereby causing device degradation.

Japanese Patent Laid-Open Publication No. 1999-003782 discloses a two naphthyl-substituted anthracene compound that can be used in an emitting layer or a hole injection layer. However, the anthracene compound is poorly soluble in a solvent, and further, an organoelectroluminescent device using the anthracene compound has unsatisfactory characteristics.

Therefore, it still needs to develop organoelectroluminescent devices which have good thermal stability and are improved in driving voltage, brightness, efficiency, and color purity characteristics.

The above information disclosed in this Background section is only for enhancement of understanding of the background of the invention and therefore it may contain information that does not form the prior art that is already known in this country to a person of ordinary skill in the art.

SUMMARY OF THE INVENTION

The present invention provides a cyclopentaphenanthrene-based compound which is adapted for both dry and wet processes, and has excellent thermal stability and good charge transport and emission characteristics, and an organoelectroluminescent device employing the same.

According to an aspect of the present invention, there is provided a cyclopentaphenanthrene-based compound represented by Formula 1 below:

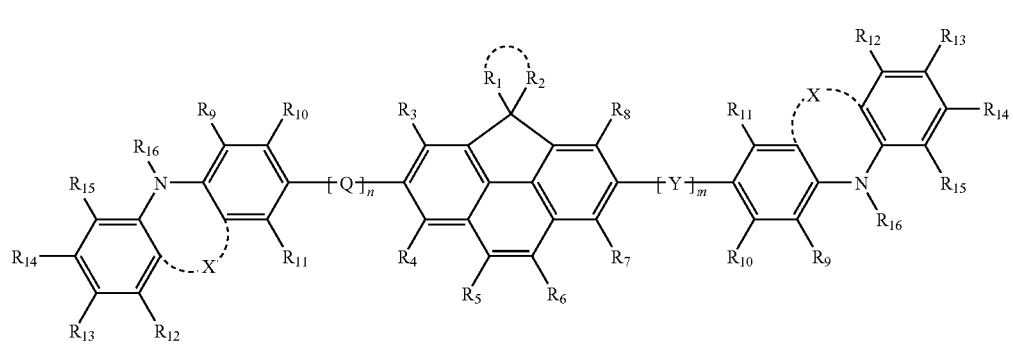

<Formula 1> wherein each Y is independently a substituted or unsubstituted C2-C30 alkylene group, a substituted or unsubstituted C6-C30 cycloalkylene group, a substituted or unsubstituted C6-C30 arylene group, a substituted or unsubstituted C2-C30 heteroarylene group, or a substituted or unsubstituted C2-C30 alkenylene group;

each Q is independently a substituted or unsubstituted C2-C30 alkylene group, a substituted or unsubstituted C6-C30 cycloalkylene group, a substituted or unsubstituted C6-C30 arylene group, a substituted or unsubstituted C2-C30 heteroarylene group, or a substituted or unsubstituted C2-C30 alkenylene group;

m is an integer of 0 to 5, and when m is an integer of 2 or more, Ys may be the same or different from each other;

n is an integer of 0 to 5, and when n is an integer of 2 or more, Qs may be the same or different from each other;

$R_1$ and $R_2$ are each independently hydrogen, halogen, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 aralkyl group, or a substituted or unsubstituted C2-C30 heteroaryl group, and $R_1$ and $R_2$ can be optionally linked together to form a substituted or unsubstituted C3-C20 aliphatic ring, a substituted or unsubstituted C5-C30 heteroaliphatic ring, a substituted or unsubstituted C6-C30 aromatic ring, or a substituted or unsubstituted C2-C30 heteroaromatic ring;

$R_3$ through $R_{16}$ are each independently hydrogen, halogen, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 aralkyl group, or a substituted or unsubstituted C2-C30 heteroaryl group; and X is a single bond, —CH=CH—, —O—, —S—, —Se—, —(CH$_2$)$_q$— where q is an integer of 1 to 5, or —C(R')(R")— where R' and R" are each independently hydrogen, halogen, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 aralkyl group, or a substituted or unsubstituted C2-C30 heteroaryl group.

In an embodiment of the present invention, the

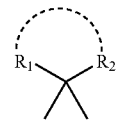

in Formula 1 may be linked together to form one represented by Formulae 2 through 5 below:

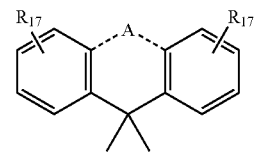

<Formula 2>

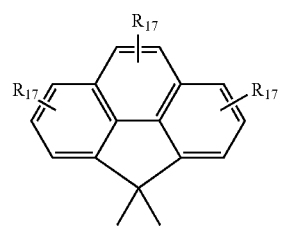

<Formula 3>

<Formula 4>

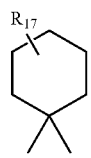

<Formula 5>

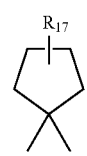

wherein each $R_{17}$ is independently hydrogen, halogen, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 aralkyl group, a substituted or unsubstituted C2-C30 heteroaryl group, —N($Z_1$)($Z_2$) or —Si($Z_3$)($Z_4$)($Z_5$) where $Z_1$, $Z_2$, $Z_3$, $Z_4$, and $Z_5$ are each independently hydrogen, a substituted or unsubstituted C1-C20 alkyl group, a substituted or unsubstituted C6-C30 aryl group, a substituted or unsubstituted C2-C30 heteroaryl group, a substituted or unsubstituted C5-C20 cycloalkyl group, or a substituted or unsubstituted C5-C30 heterocycloalkyl group; and A is a single bond, —O—, —S—, —Se—, or —($CH_2$)$_p$— where p is an integer of 1 to 5.

According to an embodiment of the present invention, the compound of Formula 1 may be selected from compounds represented by Formulae 6 through 8 below:

C6-C30 arylene group, a substituted or unsubstituted C2-C30 heteroarylene group, or a substituted or unsubstituted C2-C30 alkenylene group;

m is an integer of 0 to 5, and when m is an integer of 2 or more, Ys may be the same or different from each other;

n is an integer of 0 to 5, and when n is an integer of 2 or more, Qs may be the same or different from each other;

$R_9$ through $R_{16}$ are each independently hydrogen, halogen, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubsti-

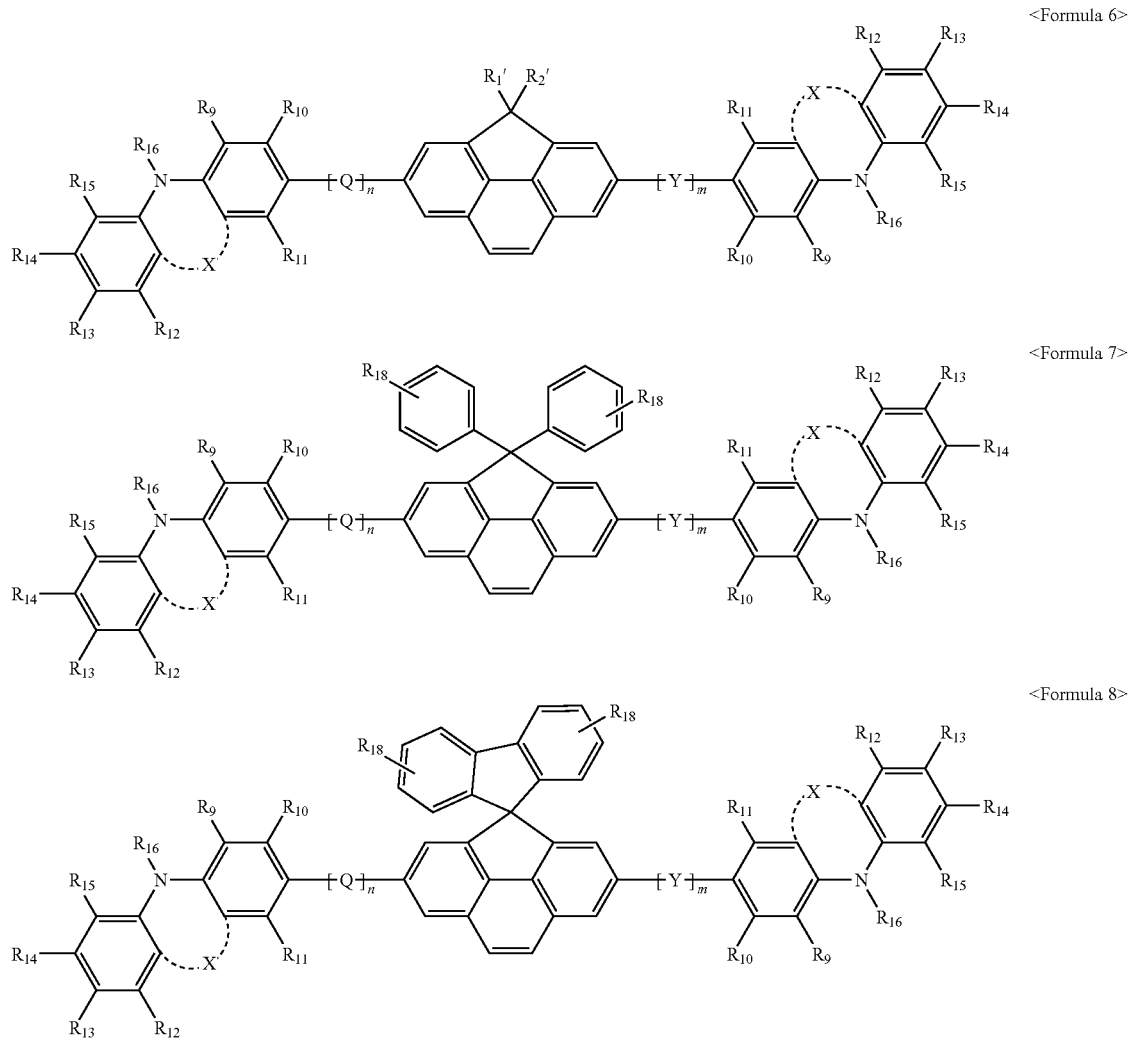

wherein each Y is independently a substituted or unsubstituted C2-C30 alkylene group, a substituted or unsubstituted C6-C30 cycloalkylene group, a substituted or unsubstituted C6-C30 arylene group, a substituted or unsubstituted C2-C30 heteroarylene group, or a substituted or unsubstituted C2-C30 alkenylene group;

each Q is independently a substituted or unsubstituted C2-C30 alkylene group, a substituted or unsubstituted C6-C30 cycloalkylene group, a substituted or unsubstituted tuted C1-C20 alkoxy group, a substituted or unsubstituted C6-C30 aryl group, a substituted or unsubstituted C6-C30 aralkyl group, or a substituted or unsubstituted C2-C30 heteroaryl group;

X is a single bond, —CH═CH—, —O—, —S—, —Se—, —($CH_2$)$_q$— where q is an integer of 1 to 5, or —C(R')(R")— where R' and R" are each independently hydrogen, halogen, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 aralkyl group, or a substituted or unsubstituted C2-C30 heteroaryl group;

$R_1'$ and $R_2'$ are each independently hydrogen, halogen, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 aralkyl group, or a substituted or unsubstituted C2-C30 heteroaryl group; and shows a photoluminescence spectrum of the compound of Formula 29 and electroluminescence spectra of Examples 2 and 3.

DETAILED DESCRIPTION OF THE INVENTION

Embodiments of the present invention will now be described more fully with reference to the accompanying drawings, in which exemplary embodiments of the invention are shown.

The present invention provides a cyclopentaphenanthrene-based compound represented by Formula 1 below:

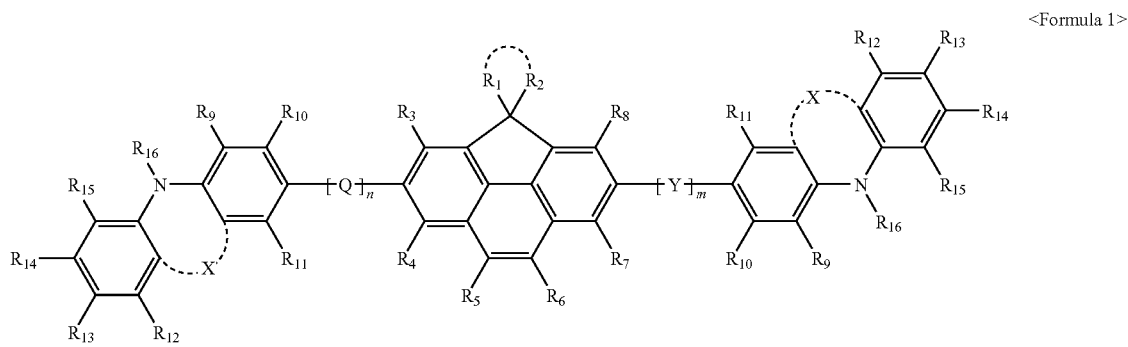

<Formula 1> each $R_{18}$ is independently hydrogen, halogen, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 aralkyl group, a substituted or unsubstituted C2-C30 heteroaryl group, $-N(Z_1)(Z_2)$ or $-Si(Z_3)(Z_4)(Z_5)$ where $Z_1, Z_2, Z_3, Z_4$, and $Z_5$ are each independently hydrogen, a substituted or unsubstituted C1-C20 alkyl group, a substituted or unsubstituted C6-C30 aryl group, a substituted or unsubstituted C2-C30 heteroaryl group, a substituted or unsubstituted C5-C20 cycloalkyl group, or a substituted or unsubstituted C5-C30 heterocycloalkyl group.

According to another aspect of the present invention, there is provided an organoelectroluminescent device including: a first electrode; a second electrode; and at least one organic layer interposed between the first electrode and the second electrode, the organic layer including the above-described organoelectroluminescent compound.

BRIEF DESCRIPTION OF THE DRAWINGS

A more complete appreciation of the invention, and many of the attendant advantages thereof, will be readily apparent as the same becomes better understood by reference to the following detailed description when considered in conjunction with the accompanying drawings in which like reference symbols indicate the same or similar components, wherein.

Figure 1A:
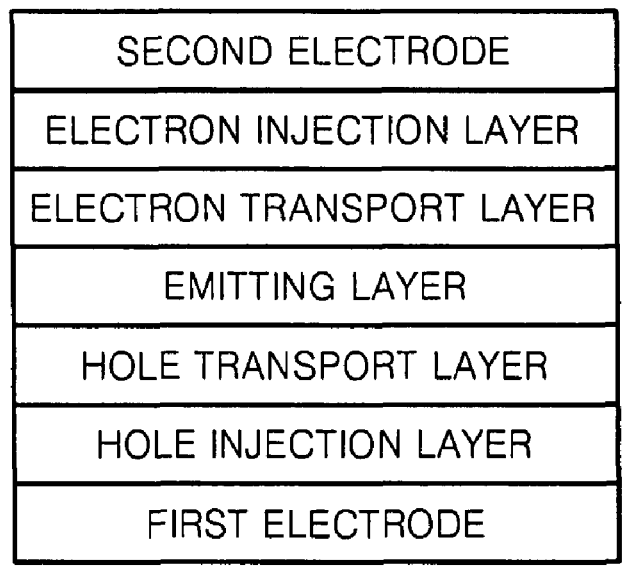
FIGS. 1A through 1C are schematic views illustrating organoelectroluminescent devices according to embodiments of the present invention.

each Q is independently a substituted or unsubstituted C2-C30 alkylene group, a substituted or unsubstituted C6-C30 cycloalkylene group, a substituted or unsubstituted C6-C30 arylene group, a substituted or unsubstituted C2-C30 heteroarylene group, or a substituted or unsubstituted C2-C30 alkenylene group;

m is an integer of 0 to 5, and when m is an integer of 2 or more, Ys may be the same or different from each other;

n is an integer of 0 to 5, and when n is an integer of 2 or more, Qs may be the same or different from each other;

$R_1$ and $R_2$ are each independently hydrogen, halogen, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 aralkyl group, or a substituted or unsubstituted C2-C30 heteroaryl group, and $R_1$ and $R_2$ can be optionally linked together to form a substituted or unsubstituted C3-C20 aliphatic ring, a substituted or unsubstituted C5-C30 heteroaliphatic ring, a substituted or unsubstituted C6-C30 aromatic ring, or a substituted or unsubstituted C2-C30 heteroaromatic ring;

$R_3$ through $R_{16}$ are each independently hydrogen, halogen, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 aralkyl group, or a substituted or unsubstituted C2-C30 heteroaryl group; and X is a single bond, —CH=CH—, —O—, —S—, —Se—, —(CH$_2$)$_q$— where q is an integer of 1 to 5, or —C(R')(R")— where R' and R" are each independently hydrogen, halogen, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 aralkyl group, or a substituted or unsubstituted C2-C30 heteroaryl group.

In the present application, when two or more are independently selected, it means that two or more may be the same or different from each other.

According to an embodiment of the present invention, the

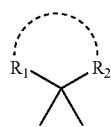

n Formula 1 may form rings represented by Formulae 2 through 5 below:

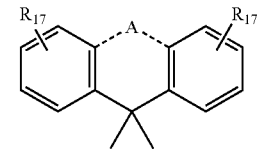
<Formula 2>

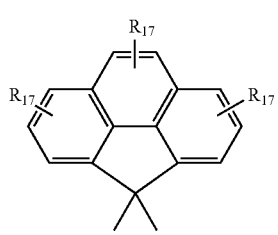
<Formula 3>

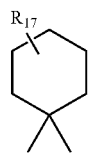
<Formula 4>

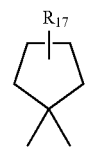
<Formula 5> wherein each R$_{17}$ is independently hydrogen, halogen, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 aralkyl group, a substituted or unsubstituted C2-C30 heteroaryl group, —N(Z$_1$)(Z$_2$) or —Si(Z$_3$)(Z$_4$)(Z$_5$) where Z$_1$, Z$_2$, Z$_3$, Z$_4$, and Z$_5$ are each independently hydrogen, a substituted or unsubstituted C1-C20 alkyl group, a substituted or unsubstituted C6-C30 aryl group, a substituted or unsubstituted C2-C30 heteroaryl group, a substituted or unsubstituted C5-C20 cycloalkyl group, or a substituted or unsubstituted C5-C30 heterocycloalkyl group; and A is a single bond, —O—, —S—, —Se—, or —(CH$_2$)$_p$— where p is an integer of 1 to 5.

The compound of Formula 1 according to the present invention may be selected from compounds represented by Formulae 6 through 8 below:

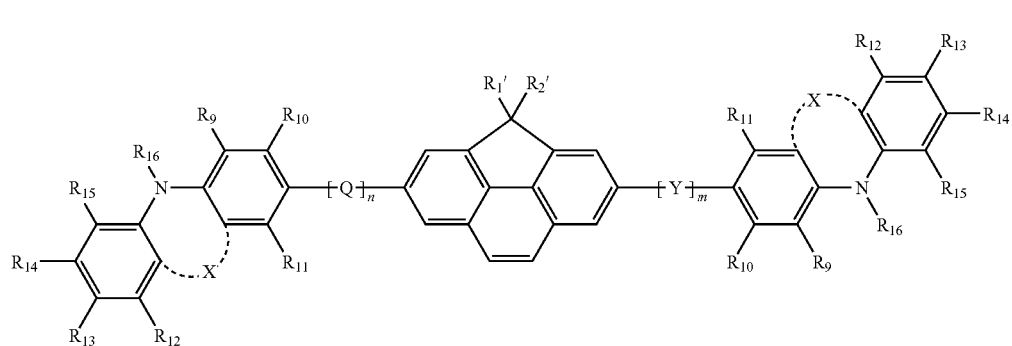
<Formula 6>

-continued

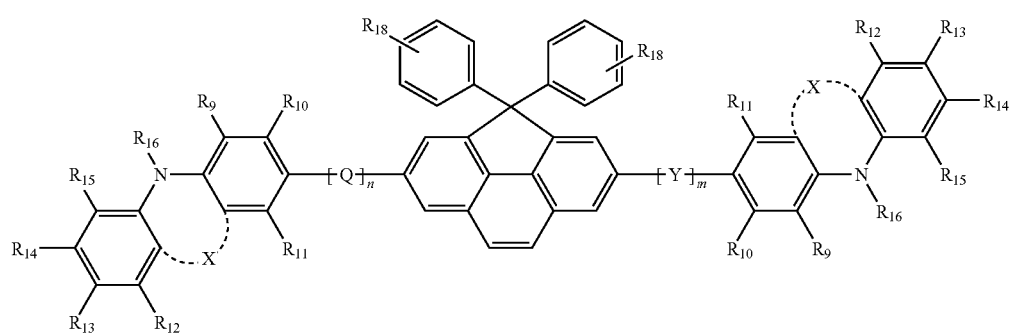

<Formula 7>

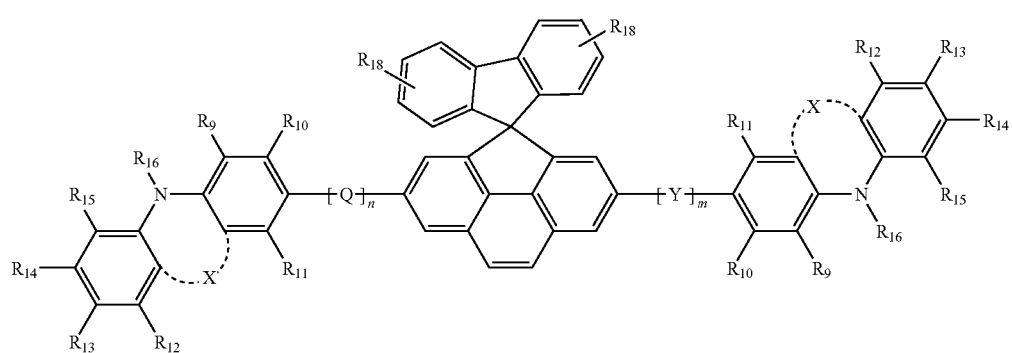

<Formula 8> wherein each Y is independently a substituted or unsubstituted C2-C30 alkylene group, a substituted or unsubstituted C6-C30 cycloalkylene group, a substituted or unsubstituted C6-C30 arylene group, a substituted or unsubstituted C2-C30 heteroarylene group, or a substituted or unsubstituted C2-C30 alkenylene group;

each Q is independently a substituted or unsubstituted C2-C30 alkylene group, a substituted or unsubstituted C6-C30 cycloalkylene group, a substituted or unsubstituted C6-C30 arylene group, a substituted or unsubstituted C2-C30 heteroarylene group, or a substituted or unsubstituted C2-C30 alkenylene group;

m is an integer of 0 to 5, and when m is an integer of 2 or more, Qs may be the same or different from each other;

n is an integer of 0 to 5, and when n is an integer of 2 or more, Ys may be the same or different from each other;

$R_9$ through $R_{16}$ are each independently hydrogen, halogen, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 aralkyl group, or a substituted or unsubstituted C2-C30 heteroaryl group;

X is a single bond, —CH=CH—, —O—, —S—, —Se—, —$(CH_2)_q$— where q is an integer of 1 to 5, or —C(R')(R")— where R' and R" are each independently hydrogen, halogen, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 aralkyl group, or a substituted or unsubstituted C2-C30 heteroaryl group;

$R_1'$ and $R_2'$ are each independently hydrogen, halogen, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 aralkyl group, or a substituted or unsubstituted C2-C30 heteroaryl group, and $R_1$ and $R_2$ can be optionally linked together to form a substituted or unsubstituted C3-C20 aliphatic ring, a substituted or unsubstituted C5-C30 heteroaliphatic ring, a substituted or unsubstituted C6-C30 aromatic ring, or a substituted or unsubstituted C2-C30 heteroaromatic ring; and each $R_{18}$ is independently hydrogen, halogen, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 aralkyl group, a substituted or unsubstituted C2-C30 heteroaryl group, —$N(Z_1)(Z_2)$ or —$Si(Z_3)(Z_4)(Z_5)$ where $Z_1, Z_2, Z_3, Z_4$, 11 and $Z_5$ are each independently hydrogen, a substituted or unsubstituted C1-C20 alkyl group, a substituted or unsubstituted C6-C30 aryl group, a substituted or unsubstituted C2-C30 heteroaryl group, a substituted or unsubstituted C5-C20 cycloalkyl group, or a substituted or unsubstituted C5-C30 heterocycloalkyl group.

In the above formulae, the "aryl group" refers to a monovalent group having an aromatic ring system and may contain two or more ring systems. The two or more ring systems may be attached or fused to each other. The "heteroaryl group" refers to an aryl group in which at least one carbon atom is substituted by at least one selected from the group consisting of N, O, S, and P.

The "cycloalkyl group" refers to an alkyl group having a ring system, and the "heterocycloalkyl group" refers to a cycloalkyl group in which at least one carbon atom is substituted by at least one selected from the group consisting of N, O, S, and P.

In the above formulae, the alkyl group, the alkoxy group, the aryl group, the heteroaryl group, the cycloalkyl group, and the heterocycloalkyl group may be substituted by at least one substituent selected from the group consisting of —F; —Cl; —Br; —CN; —NO$_2$; —OH; a C1-C20 alkyl group which is unsubstituted or substituted by —F, —Cl, —Br, —CN, —NO$_2$, or —OH; a C1-C20 alkoxy group which is unsubstituted or substituted by —F, —Cl, —Br, —CN, —NO$_2$, or —OH; a C6-C30 aryl group which is unsubstituted or substituted by a C1-C20 alkyl group, a C1-C20 alkoxy group, —F, —Cl, —Br, —CN, —NO$_2$, or —OH; a C2-C30 heteroaryl group which is unsubstituted or substituted by a C1-C20 alkyl group, a C1-C20 alkoxy group, —F, —Cl, —Br, —CN, —NO$_2$, or —OH; a C5-C20 cycloalkyl group which is unsubstituted or substituted by a C1-C20 alkyl group, a C1-C20 alkoxy group, —F, —Cl, —Br, —CN, —NO$_2$, or —OH; a C5-C30 heterocycloalkyl group which is unsubstituted or substituted by a C1-C20 alkyl group, a C1-C20 alkoxy group, —F, —Cl, —Br, —CN, —NO$_2$, or —OH; and a group represented by —N(G$_6$)(G$_7$) where, G$_6$ and G$_7$ are each independently hydrogen; a C1-C10 alkyl group; or a C6-C30 aryl group which is substituted by a C1-C10 alkyl group.

In more detail, R$_1$ through R$_{16}$ are each independently selected from the group consisting of hydrogen, halogen, a cyano group, a hydroxyl group, a C1-C10 alkyl group, a C1-C10 alkoxy group, and a substituted or unsubstituted group as follows: a phenyl group, a biphenyl group, a pentalenyl group, an indenyl group, a naphthyl group, a biphenylenyl, an anthracenyl group, an azulenyl group, a heptalenyl group, an acenaphthylenyl group, a phenalenyl group, a fluorenyl group, a methylanthryl group, a phenanthrenyl group, a triphenylenyl group, a pyrenyl group, a chrysenyl group, an ethyl-chrysenyl group, a picenyl group, a perylenyl group, a chloroperylenyl group, a pentaphenyl group, a pentacenyl group, a tetraphenylenyl group, a hexaphenyl group, a hexacenyl group, a rubicenyl group, a coronenyl group, a trinaphthylenyl group, a heptaphenyl group, a heptacenyl group, a pyranthrenyl group, an ovalenyl group, a carbazolyl group, a thiophenyl group, an indolyl group, a purinyl group, a benzimidazolyl group, a quinolinyl group, a benzothiophenyl group, a parathiazinyl group, a pyrrolyl group, a pyrazolyl group, an imidazolyl group, an imidazolinyl group, an oxazolyl group, a thiazolyl group, a triazolyl group, a tetrazolyl group, an oxadiazolyl group, a pyridinyl group, a pyridazinyl group, a pyrimidinyl group, a pyrazinyl group, a thianthrenyl group, a cyclopentyl group, a cyclohexyl group, an oxiranyl group, a pyrrolidinyl group, a pyrazolidinyl group, an imidazolidinyl group, a piperidinyl group, a piperazinyl group, a morpholinyl group, a di(C6-C30 aryl)amino group, a tri(C6-C30 aryl)silyl group, and derivatives thereof.

As used herein, the term "derivative(s)" refers to the above-illustrated group(s) wherein at least one hydrogen is substituted by a substituent as described above.

The compound according to the embodiment of the present invention may be selected from the group consisting of compounds represented by Formulae 9 through 28 below, but is not limited to:

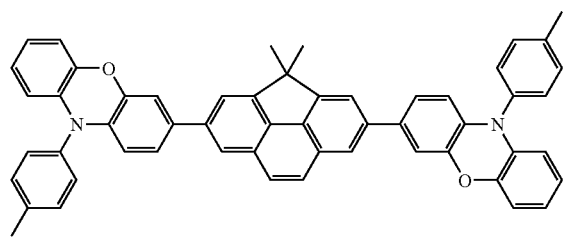

<Formula 9>

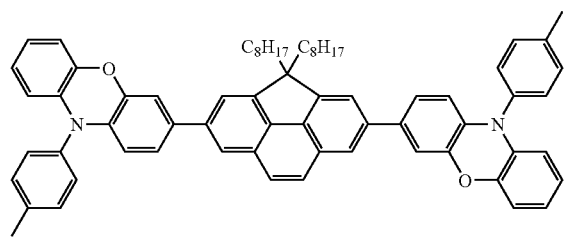

<Formula 10>

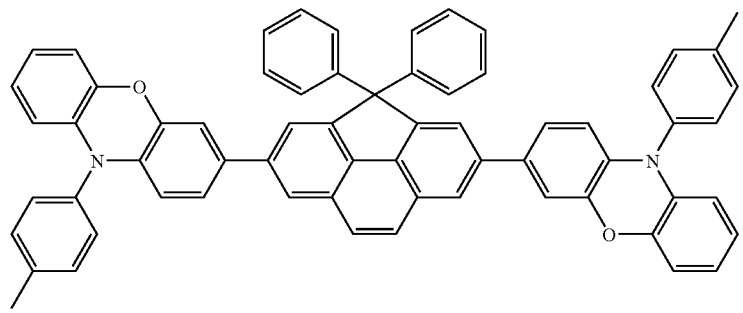

<Formula 11>

-continued
<Formula 12>
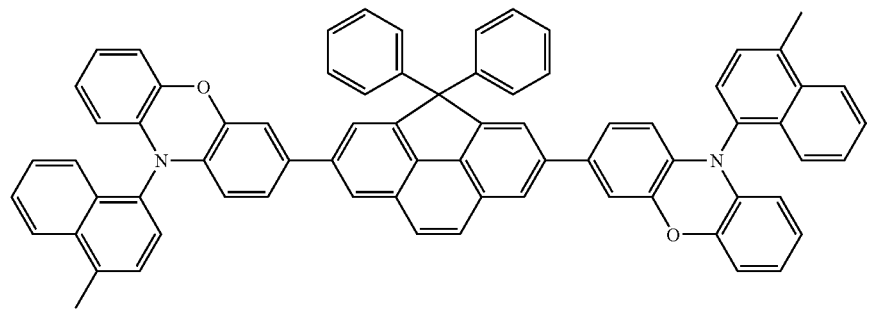
<Formula 13>
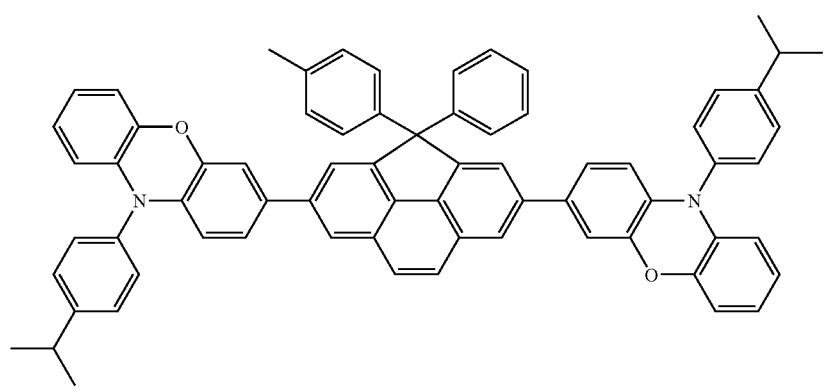
<Formula 14>
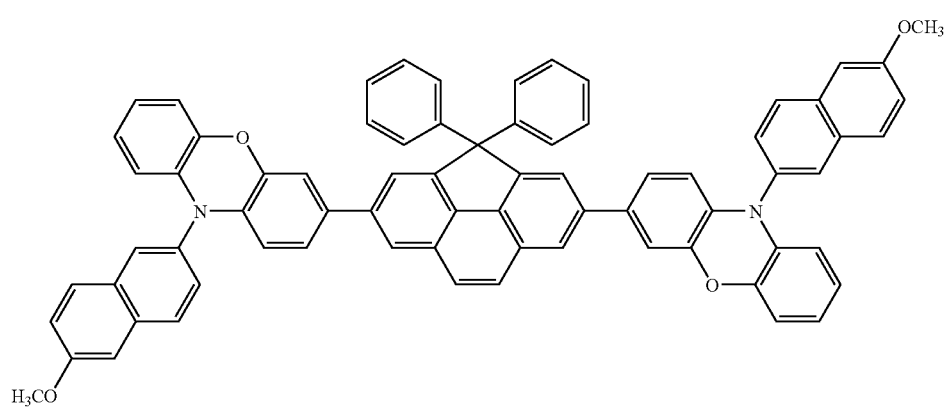
<Formula 15>
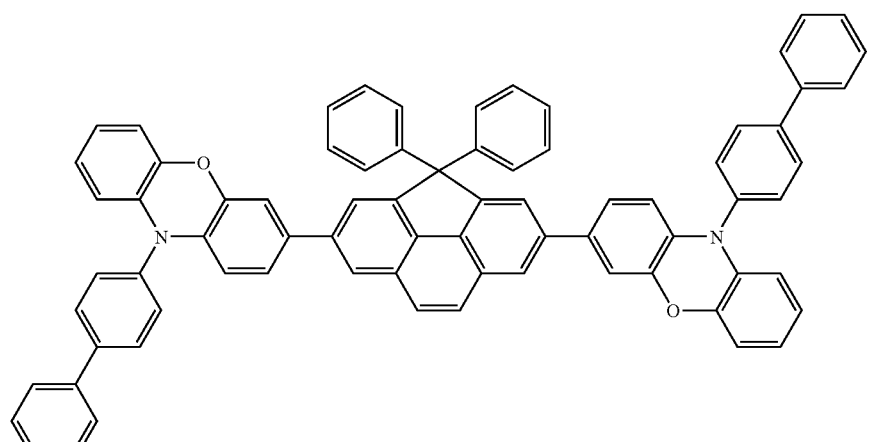

The compound of Formula 1 according to the present invention can be synthesized using a common synthesis method. For an exemplary synthesis procedure of the compound according to the embodiment of the present invention, reference will be made to the reaction schemes in the following synthesis examples.

The present invention also provides an organoelectroluminescent device including a first electrode, a second electrode, and an organic layer interposed between the first electrode and the second electrode, the organic layer including at least one compound represented by Formula 1 above.

The compound of Formula 1 is suitable for an organic layer of an organoelectroluminescent device, in particular an emitting layer, a hole injection layer, or a hole transport layer.

The organoelectroluminescent device according to the present invention includes a compound which has good solubility and thermal stability and can form a stable organic layer, and thus, can show a good driving voltage and enhanced emission characteristics (e.g., color purity), unlike a conventional organoelectroluminescent device including a less stable organic layer when manufactured using a solution coating process.

The organoelectroluminescent device according to the present invention can be variously structured. That is, the organoelectroluminescent device may further include at least one layer selected from the group consisting of a hole injection layer, a hole transport layer, a hole blocking layer, an electron blocking layer, an electron transport layer, and an electron injection layer, between the first electrode and the second electrode.

Figure 1B:
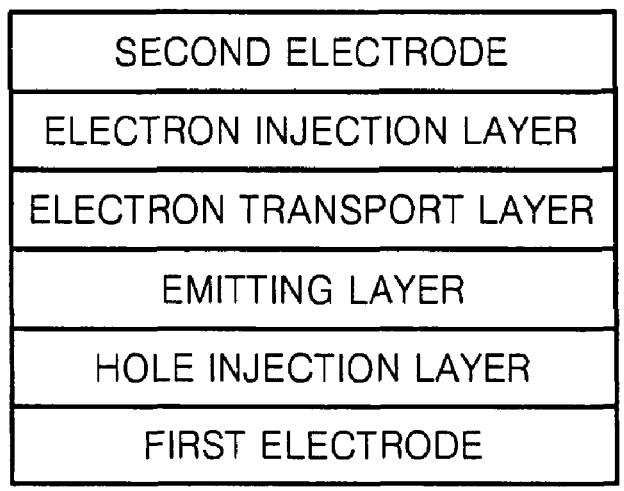
Figure 1C:
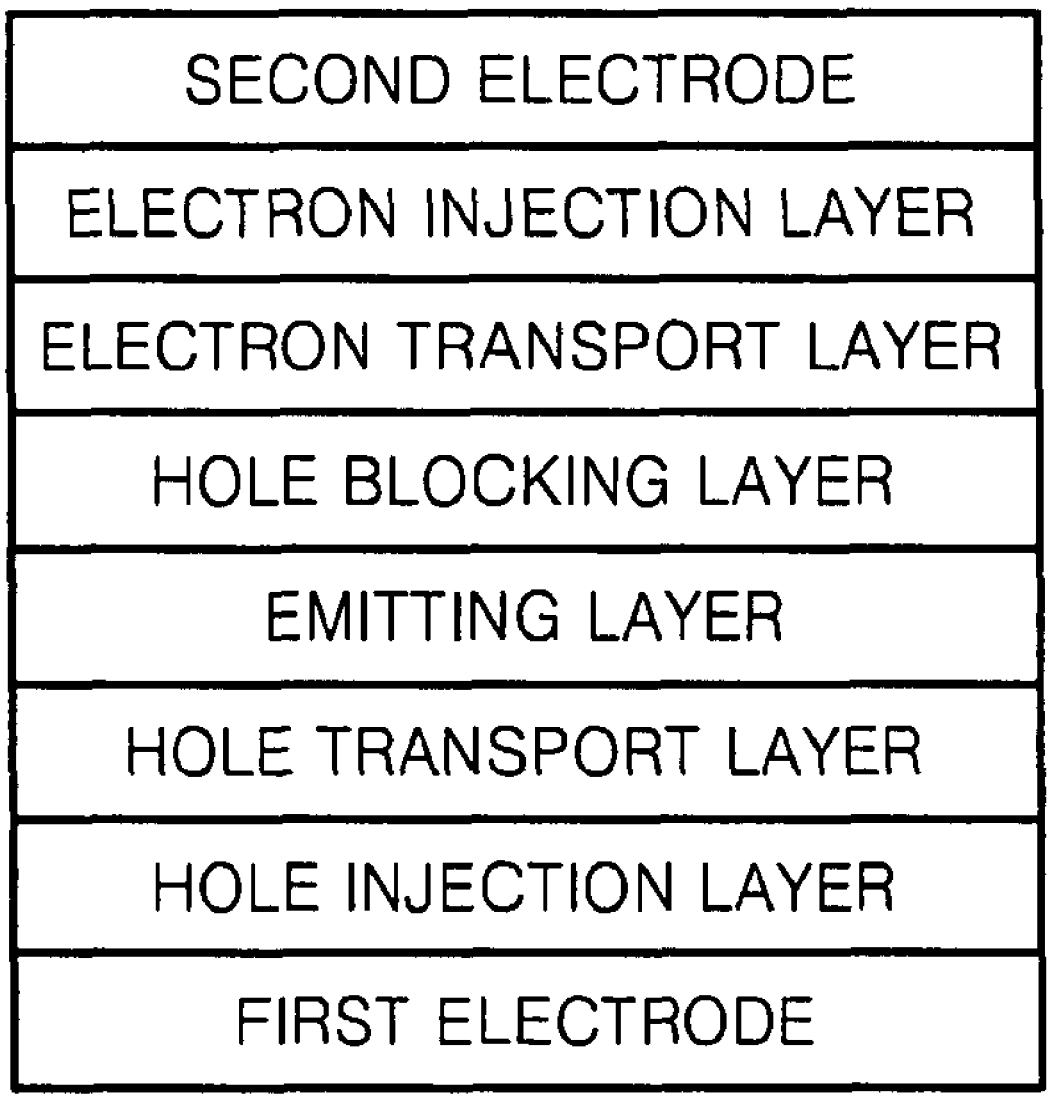

In more detail, organoelectroluminescent devices according to embodiments of the present invention are illustrated in FIGS. 1A, 1B, and 1C. Referring to FIG. 1A, an organoelectroluminescent device has a stacked structure of first electrode/hole injection layer/hole transport layer/emitting layer/electron transport layer/electron injection layer/second electrode. Referring to FIG. 1B, an organoelectroluminescent device has a stacked structure of first electrode/hole injection layer/emitting layer/electron transport layer/electron injection layer/second electrode. Referring to FIG. 1C, an organoelectroluminescent device has a stacked structure of first electrode/hole injection layer/hole transport layer/emitting layer/hole blocking layer/electron transport layer/electron injection layer/second electrode. Here, at least one of the emitting layer, the hole injection layer, and the hole transport layer may include a compound according to an embodiment of the present invention.

An emitting layer of the organoelectroluminescent device according to the present invention may include a red, green, blue, or white phosphorescent or fluorescent dopant. The phosphorescent dopant may be an organometallic compound including at least one element selected from the group consisting of Ir, Pt, Os, Ti, Zr, Hf, Eu, Tb, and Tm.

Hereinafter, an exemplary method of manufacturing an organoelectroluminescent device according to an embodiment of the present invention will be described with reference to FIG. 1C.

First, a first electrode is formed on a substrate by a deposition or sputtering process using a first electrode material with a high work function. The first electrode may be an anode. Here, the substrate may be a substrate commonly used in organoelectroluminescent devices. Preferably, the substrate may be a glass or transparent plastic substrate which is excellent in mechanical strength, thermal stability, transparency, surface smoothness, handling property, and water repellency. The first electrode material may be a material with transparency and good conductivity, e.g., indium tin oxide (ITO), indium zinc oxide (IZO), tin oxide ($SnO_2$), or zinc oxide (ZnO).

Next, a hole injection layer (HIL) may be formed on the first electrode using various methods such as vacuum deposition, spin-coating, casting, or Langmuir-Blodgett (LB) method.

In the case of forming the hole injection layer using a vacuum deposition process, the deposition conditions vary according to the type of a hole injection layer material, the structure and thermal characteristics of the hole injection layer, etc. However, it is preferred that the hole injection layer should be deposited to a thickness of 10 Å to 5 μm at a deposition rate of 0.01 to 100 Å/sec, at a temperature of 100 to 500° C., in a vacuum level of $10^{-8}$ to $10^{-3}$ torr.

In the case of forming the hole injection layer using a spin-coating process, the coating conditions vary according to the type of a hole injection layer material, the structure and thermal characteristics of the hole injection layer, etc. However, it is preferred that the spin-coating should be performed at a coating speed of about 2,000 to 5,000 rpm, and, after the spin-coating, a thermal treatment should be performed at a temperature of about 80 to 200° C. for the purpose of solvent removal.

The hole injection layer material may be a compound of Formula 1 as described above. In addition, the hole injection layer material may be a known hole injection material, e.g., a phthalocyanine compound (e.g., copper phthalocyanine) disclosed in U.S. Pat. No. 4,356,429 which is incorporated herein by reference, a Starburst-type amine derivative (e.g., TCTA, m-MTDATA, or m-MTDAPB) disclosed in *Advanced Material*, 6, p. 677 (1994) which is incorporated herein by reference, or a soluble conductive polymer, e.g., polyaniline/dodecylbenzenesulfonic acid (Pani/DBSA), poly(3,4-ethylenedioxythiophene)/poly(4-styrenesulfonate) (PEDOT/PSS), polyaniline/camphor sulfonic acid (Pani/CSA), or polyaniline/poly(4-styrenesulfonate) (PANI/PSS).

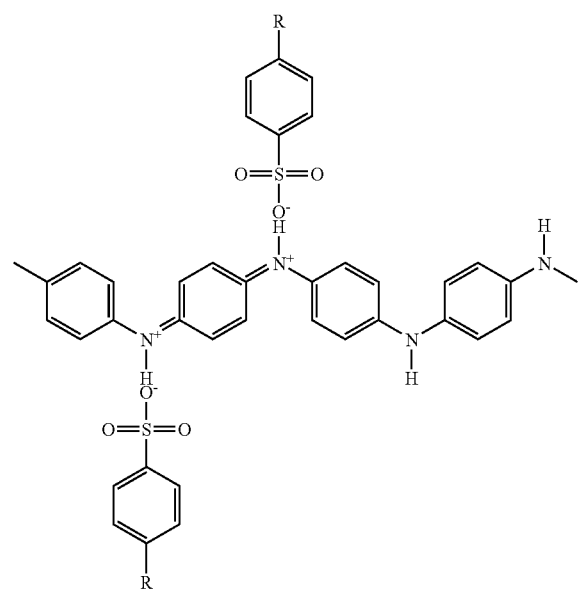

Pani/DBSA

-continued

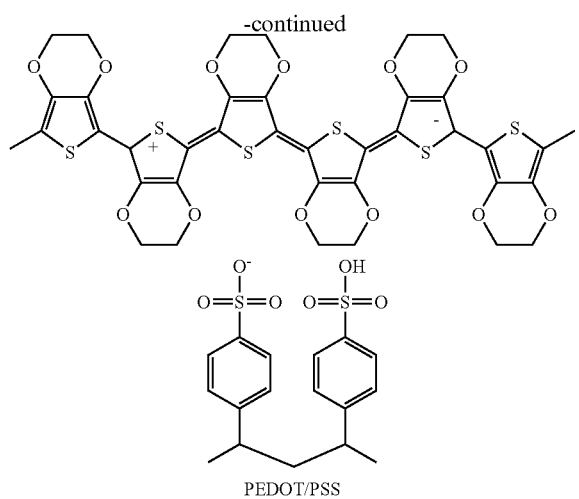

PEDOT/PSS

The hole injection layer may be formed to a thickness of about 100 to 10,000 Å, preferably 100 to 1,000 Å. If the thickness of the hole injection layer is less than 100 Å, hole injection characteristics may be lowered. On the other hand, if the thickness of the hole injection layer exceeds 10,000 Å, a driving voltage may be increased.

Next, a hole transport layer (HTL) may be formed on the hole injection layer using various methods such as vacuum deposition, spin-coating, casting, or LB method. In the case of forming the hole transport layer using vacuum deposition or spin-coating, the deposition or coating conditions vary according to the type of a used compound, but are generally almost the same as those for the formation of the hole injection layer.

A hole transport layer material may be a compound of Formula 1 as described above. In addition, the hole transport layer material can be a known hole transport material, e.g., a carbazole derivative such as N-phenylcarbazole or polyvinylcarbazole; an amine derivative having an aromatic fused ring such as N,N'-bis(3-methylphenyl)-N,N'-diphenyl-[1,1-biphenyl]-4,4'-diamine (TPD) or N,N'-di(naphthalene-1-yl)-N, N'-diphenylbenzidine (α-NPD), etc.

The hole transport layer may be formed to a thickness of about 50 to 1,000 Å, preferably 100 to 600 Å. If the thickness of the hole transport layer is less than 50 Å, hole transport characteristics may be lowered. On the other hand, if the thickness of the hole transport layer exceeds 1,000 Å, a driving voltage may be increased.

Next, an emitting layer (EML) may be formed on the hole transport layer using vacuum deposition, spin-coating, casting, or LB method. In the case of forming the emitting layer using vacuum deposition or spin-coating, the deposition or coating conditions vary according to the type of a used compound, but are generally almost the same as those for the formation of the hole injection layer.

The emitting layer may include a compound of Formula 1 as described above. Here, a known fluorescent host material suitable for the compound of Formula 1 or a known dopant material may be used together with the compound of Formula 1. The compound of Formula 1 may be used as a phosphorescent host alone or in combination with 4,4'-N,N'-dicarbazole-biphenyl (CBP), poly(n-vinylcarbazole) (PVK), etc. As a phosphorescent dopant, there may be used a red phosphorescent dopant (e.g., PtOEP, RD 61 (UDC)), a green phosphorescent dopant (e.g., Ir(PPy)3 (PPy=2-phenylpyridine)), or a blue phosphorescent dopant (e.g., $F_2Irpic$).

When the compound of Formula 1 is used as a dopant, the doping concentration of the dopant is not particularly limited. Generally, the content of the dopant is 0.01 to 15 parts by weight based on 100 parts by weight of a host. When the compound of Formula 1 is used as a single host, the doping concentration of a dopant is not particularly-limited. Generally, the content of a dopant is 0.01 to 15 parts by weight based on 100 parts by weight of the host. When the compound of Formula 1 is used as a host in combination with another host, the content of the compound of Formula 1 is 30-99 parts by weight based on the total weight (100 parts by weight) of the hosts.

The emitting layer may be formed to a thickness of about 100 to 1,000 Å, preferably 200 to 600 Å. If the thickness of the emitting layer is less than 100 Å, emission characteristics may be lowered. On the other hand, if the thickness of the emitting layer exceeds 1,000 Å, a driving voltage may be increased.

In a case where the emitting layer includes a phosphorescent dopant, a hole blocking layer (HBL) may be formed on the emitting layer using vacuum deposition, spin-coating, casting, or LB method, in order to prevent the diffusion of triplet excitons or holes into an electron transport layer. In the case of forming the hole blocking layer using vacuum deposition or spin coating, the deposition or coating conditions vary according to the type of a used compound, but are generally almost the same as those for the formation of the hole injection layer. An available hole blocking material may be an oxadiazole derivative, a triazole derivative, a phenanthroline derivative, BCP, an aluminum complex, etc.

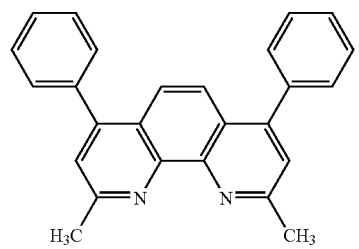

Phenanthroline-containing organic compound

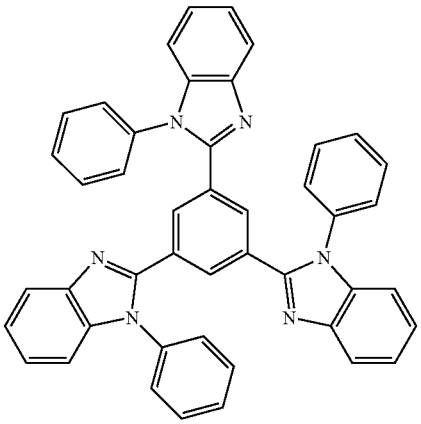

Imidazole-containing organic compound

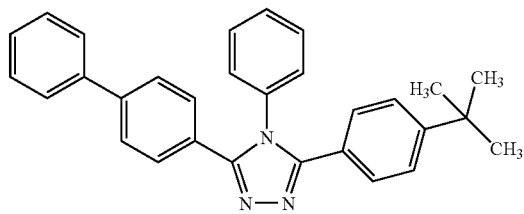

Triazole-containing organic compound

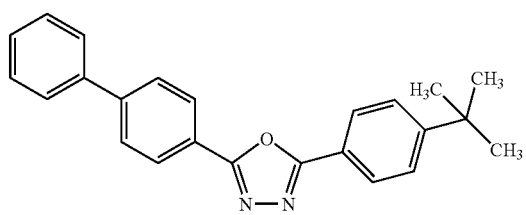

Oxadiazole-containing compound

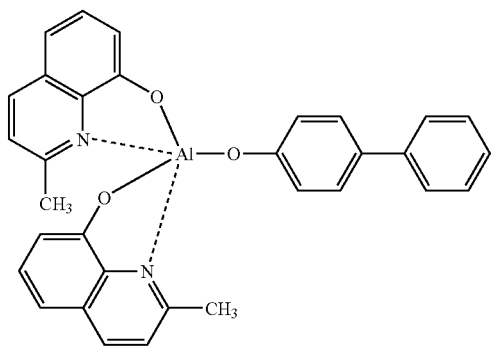

BAlq

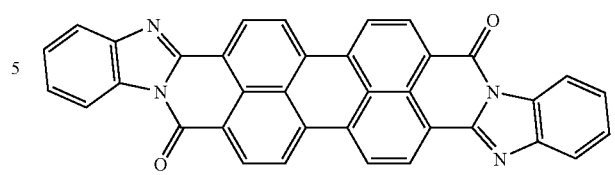

Perylene-based compound

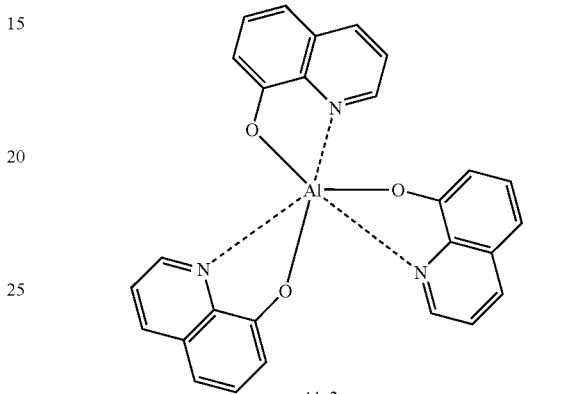

Alq3

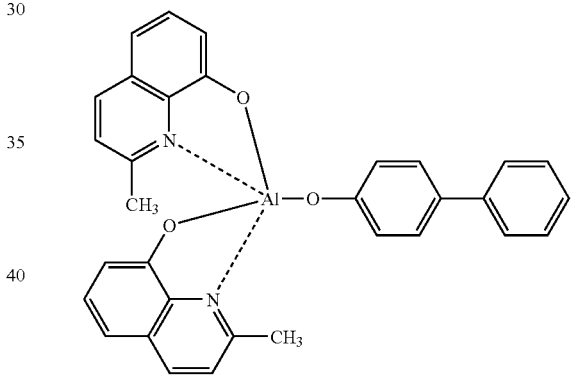

BAlq

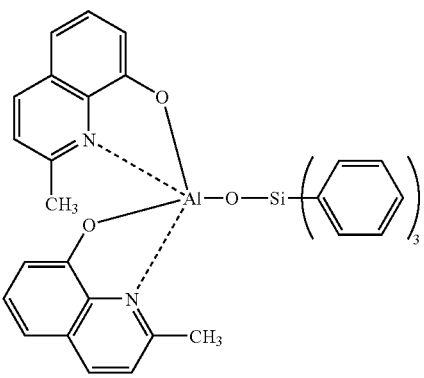

SAlq

The hole blocking layer may be formed to a thickness of about 50 to 1,000 Å, preferably 100 to 300 Å. If the thickness of the hole blocking layer is less than 50 Å, hole blocking characteristics may be lowered. On the other hand, if the thickness of the hole blocking layer exceeds 1,000 Å, a driving voltage may be increased.

Next, an electron transport layer (ETL) may be formed using various methods such as vacuum deposition, spin-coating, or casting. In the case of forming the electron transport layer using vacuum deposition or spin-coating, the deposition or coating conditions vary according to the type of a used compound, but are generally almost the same as those for the formation of the hole injection layer. An electron transport layer material serves to stably transport electrons from an electron donor electrode (a cathode) and may be a known material such as an oxazole-based compound, an isoxazole-based compound, a triazole-based compound, an isothiazole-based compound, an oxadiazole-based compound, a thiadiazole-based compound, a perylene-based compound, an aluminum complex (e.g.: Alq3 (tris(8-quinolinolato)-aluminum), BAlq, SAlq, or Almq3), a gallium complex (e.g.: Gaq'2OPiv, Gaq'2OAc, 2(Gaq'2)), etc.

-continued

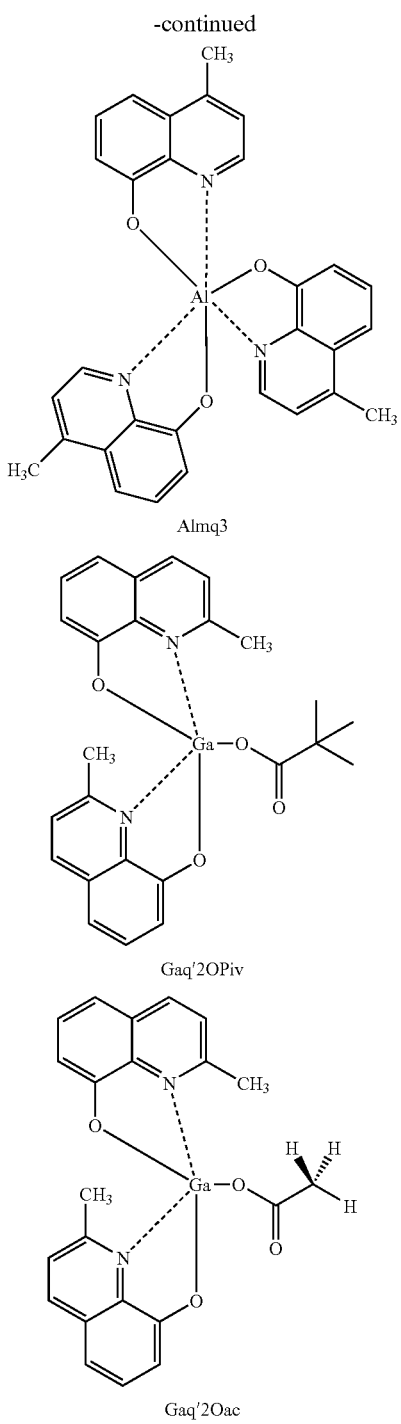

Almq3

Gaq'2OPiv

Gaq'2Oac

-continued

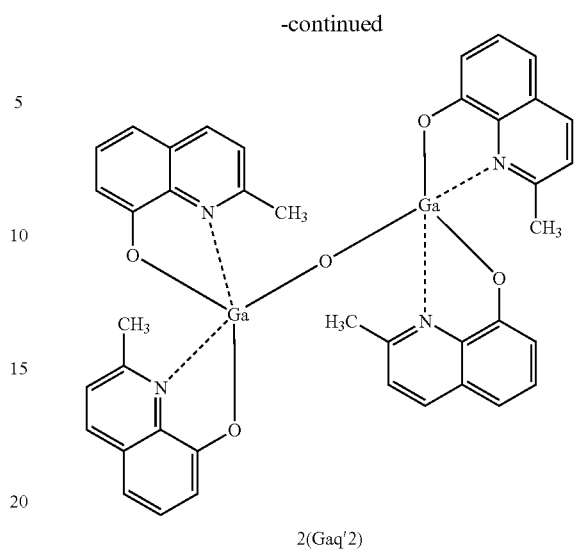

2(Gaq'2)

The electron transport layer may be formed to a thickness of about 100 to 1,000 Å, preferably 200 to 500 Å. If the thickness of the electron transport layer is less than 100 Å, electron transport characteristics may be lowered. On the other hand, if the thickness of the electron transport layer exceeds 1,000 Å, a driving voltage may be increased.

An electron injection layer (EIL) may be formed on the electron transport layer in order to facilitate the injection of electrons from a cathode into the emitting layer. An electron injection layer material is not particularly limited.

The electron injection layer material may be selected from known materials such as LiF, NaCl, CsF, $Li_2O$, or BaO. The deposition conditions of the electron injection layer vary according to the type of a used compound, but are generally almost the same as those for the formation of the hole injection layer.

The electron injection layer may be formed to a thickness of about 1 to 100 Å, preferably 5 to 50 Å. If the thickness of the electron injection layer is less than 1 Å, electron injection characteristics may be lowered. On the other hand, if the thickness of the electron injection layer exceeds 100 Å, a driving voltage may be increased.

Finally, a second electrode may be formed on the electron injection layer using vacuum deposition or sputtering. The second electrode may be used as a cathode. A material for forming the second electrode may be metal or alloy with a low work function, an electroconductive compound, or a mixture thereof. For example, the second electrode material may be lithium (Li), magnesium (Mg), aluminum (Al), aluminum-lithium (Al—Li), calcium (Ca), magnesium-indium (Mg—In), magnesium-silver (Mg—Ag), etc. The second electrode may also be a transmissive cathode formed of ITO or IZO to provide a front-emission type device.

Hereinafter, the present invention will be described more specifically with reference to the following working examples. However, the following working examples are only for illustrative purposes and are not intended to limit the scope of the invention.

EXAMPLES

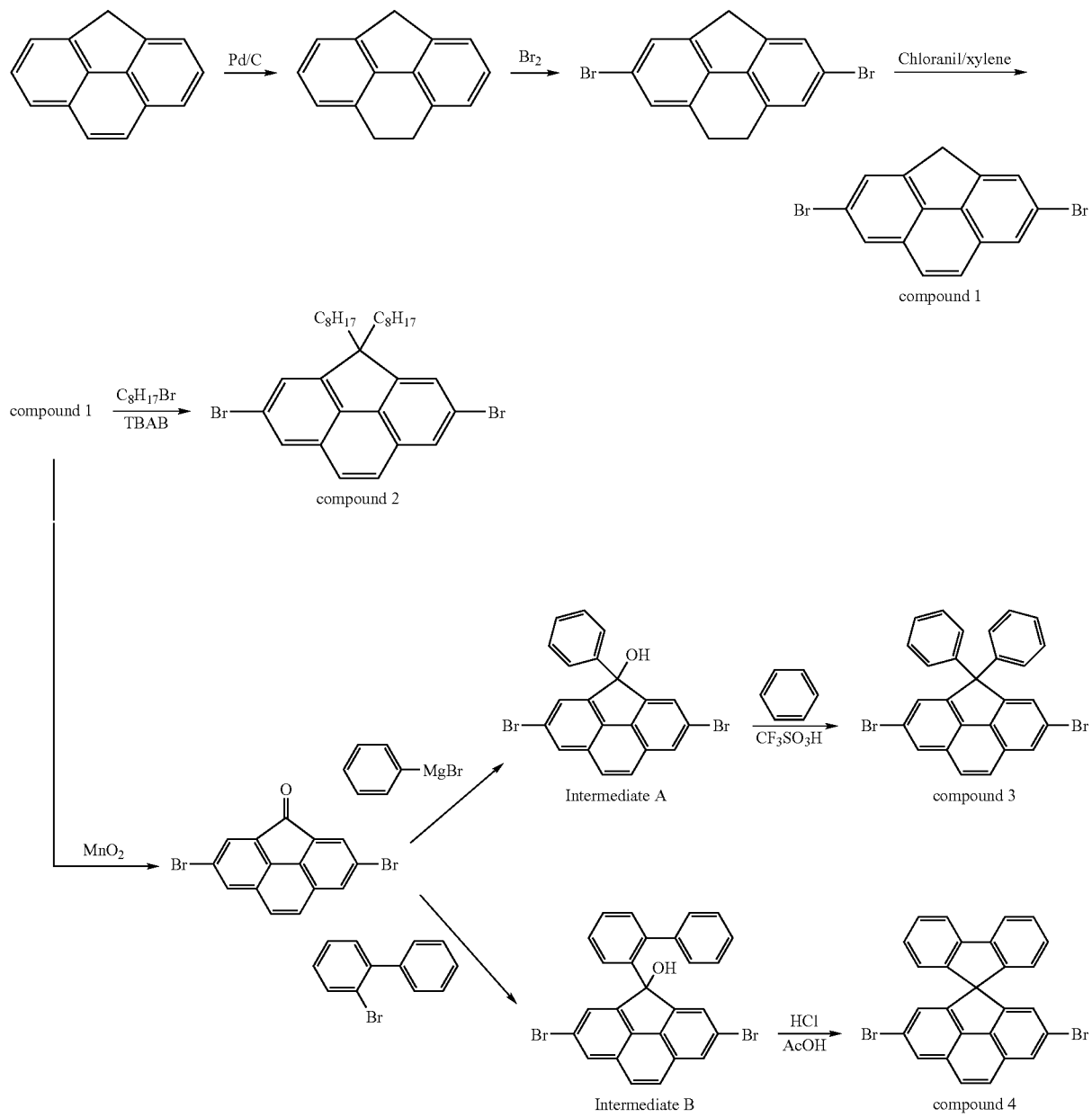

Synthesis Example 1

1) Synthesis of 8,9-dihydro-4H-cyclopenta[def]phenanthrene 4H-cyclopenta[def]phenanthrene (4.75 g, 25 mmol) was put into a Par reactor bottle, and EtOH (200 ml) was added thereto. 5% Pd/C (3.99 g) was added to the reaction solution, and the resultant solution was incubated under a hydrogen pressure of 40 psi for 24 hours. After the reaction was terminated, the reaction solution was filtered, and the filtrate was concentrated under a reduced pressure to give a white product (4.32 g, 90%).

$^1$H NMR (300 MHz, CDCl$_3$, δ): 7.36(2H, d), 7.21(2H, t), 7.12(2H, d), 3.90(2H, s), 3.16(4H, s)

2) Synthesis of 2,6-dibromo-8,9-dihydro-4H-cyclopenta[def]phenanthrene 8,9-dihydro-4H-cyclopenta[def]phenanthrene (4.42 g, 23 mmol) was put into a 250 ml round bottom flask (RBF), and CCl$_4$ (100 ml) was added thereto and dissolved therein. The reaction mixture was cooled to 0° C., and Br$_2$ (7.72 g, 48 mmol) was dropwise added thereto. The reaction solution was incubated for 4 hours and a 10% NaSO$_3$ solution was added thereto. The organic phase was separated, concentrated under a reduced pressure, and recrystallized from n-hexane to obtain 4.45 g (55%) of a 2,6-dibromo-8,9-dihydro-4H-cyclopenta[def]phenanthrene compound.

$^1$H NMR (300 MHz, CDCl$_3$, δ): 7.48(2H, s), 7.28(2H, s), 3.85(2H, s), 3.10(4H, s)

3) Synthesis of Compound 1

2,6-dibromo-8,9-dihydro-4H-cyclopenta[def]phenanthrene (4.45 g, 12.7 mmol) in a 250 ml round bottom flask was dissolved with xylene, and o-chloranil (4.15 g) was added thereto at room temperature. The reaction mixture was heated and refluxed in an oil bath for 72 hours. After the reaction was terminated, the reaction solution was cooled and concentrated under a reduced pressure. The residue was purified by silica gel column chromatography (developing solvent: n-hexane) to give a compound 1 (3.6 g, 81%).

$^1$H NMR (300 MHz, CDCl$_3$, δ): 7.98 (2H, s), 7.79(2H, s), 7.73(2H, s), 4.28(2H, s)

4) Synthesis of Compound 2

2,6-dibromo-4H-cyclopenta[def]phenanthrene (2.6 g, 7.7 mmol) and octyl bromide (3.6 g, 18.5 mmol) in a 50 ml round bottom flask were dissolved with toluene (10 ml), and tetrabutylammoniumbromide (TBAB) (0.125 g, 0.385 mmol) was added thereto. A solution of NaOH (3.1 g, 77 mmol) in water (50 ml) was added to the reaction mixture, and the resultant solution was refluxed for two days. After the reaction was terminated, the reaction solution was extracted with chloroform. The organic phase was dried over MgSO$_4$, concentrated, and purified by silica gel column chromatography (eluent: n-hexane). The eluate was distilled under a reduced pressure to remove unreacted octyl bromide, thereby giving a compound 2 (3.6 g, 80%).

$^1$H NMR (300 MHz, CDCl$_3$, δ): 7.98(2H, s), 7.79(2H, s), 7.73(2H, s), 1.93(m, 4H), 1.21(m, 20H), 0.87(m, 6H), 0.65 (broad s, 4H)

5) Synthesis of Material 1(Formula 10)

1.14 g (1 eq, 2.0 mmol) of the compound 2, 0.8 g (1 eq, 2.0 mmol) of 3-(4,4,5,5-tetramethyl-[1,3,2]dioxaborolane-2-yl)-10-p-tolyl-10H-phenoxazine, 0.23 g (0.1 eq, 0.2 mmol) of tetrakis(triphenylphosphine)palladium(0), 1 ml (1 eq, 2.0 mmol) of 2M K$_2$CO$_3$, and 0.65 g (1 eq, 2.0 mmol) of tetrabutylammoniumbromide were put into a 100 ml round bottom flask under an argon gas atmosphere, and THF (50 ml) and toluene (20 ml) were added thereto. The reaction mixture was refluxed at 100° C. for 16 hours. When the reaction solution turned dark brown, water was added, and the resultant solution was extracted with ethylacetate. The extracted organic phase was dried over anhydrous magnesium sulfate and filtered to remove a solvent. The residue was dissolved in a trace amount of toluene and purified on a silica gel column. The resultant solid was recrystallized from toluene and methanol to give a material 1 represented by Formula 10 (0.95 g, 50%).

$^1$H NMR (300 MHz, CDCl$_3$, δ): 8.11(s, 2H), 7.98(s, 2H), 7.81(s, 2H), 7.25-5.87(m, 22H), 2.51(s, 3H), 1.93(m, 4H), 1.21(m, 20H), 0.87(m, 6H), 0.65(broad s, 4H).

Synthesis Example 2

1) Synthesis of 2,6-dibromo-cyclopenta[def]phenanthren-4-one

Benzene (200 ml) was put into a 250 ml round bottom flask, and the compound 1 (3.6 g, 10.4 mmol) was added thereto. MnO$_2$ (150 g) was added to the reaction mixture, and the resultant mixture was heated and refluxed in an oil bath for 18 hours. After the reaction was terminated, the reaction solution was filtered to remove MnO$_2$, and sufficiently washed with CHCl$_3$, THF, and MeOH in sequence. The filtrate was concentrated under a reduced pressure and the residue was recrystallized from acetone to give the titled compound (1.45 g, 39%).

$^1$H NMR (300 MHz, CDCl$_3$, δ): 8.08(2H, s), 7.89(2H, s), 7.74(2H, s)

2) Synthesis of Intermediate A 2,6-dibromo-cyclopenta[def]phenanthrene-4-one (1.0 g, 2.76 mmol) was dissolved in dry ether (30 ml) and THF (10 ml), and phenylmagnesiumbromide (3.0M in ether) was gradually added thereto under a nitrogen gas atmosphere. The reaction mixture was refluxed for three hours, and water was added thereto so that the reaction was terminated. The resultant solution was adjusted to pH of 3-4 with a 1N-HCl solution and extracted with ethyl ether. The organic phase was dried over anhydrous sodium sulfate, filtered, and concentrated under a reduced pressure. The resultant solid was purified by silica gel column chromatography to give 0.79 g (65%) of an intermediate A as a solid phase.

3) Synthesis of Compound 3

0.79 g (1.79 mmol) of the intermediate A was dissolved in 20 ml of dry benzene, and 0.48 ml (5.38 mmol, 3 eq.) of trifluoromethanesulfonic acid was dropwise added thereto. The reaction mixture was incubated at 80° C. for two hours. The resultant solution was diluted with water and extracted with ethylacetate. The organic phase was dried over anhydrous sodium sulfate, filtered, and concentrated under a reduced pressure. The resultant solid was purified by silica gel column chromatography and recrystallized from a EtOAc-Hex mixed solvent to give 0.65 g (63%) of a compound 3 as a solid phase. $^1$H NMR (300 MHz, CDCl$_3$, δ): 7.22-7.26 (m, 10H), 7.70 (s, 2H), 7.80 (s, 3H), 8.00 (s, 2H)

4) Synthesis of Material 2(Formula 11)

1.0 g (1 eq, 2.0 mmol) of the compound 3, 0.8 g (1 eq, 2.0 mmol) of 3-(4,4,5,5-tetramethyl-[1,3,2]dioxaborolane-2-yl)-10-p-tolyl-10H-phenoxazine, 0.23 g (0.1 eq, 0.2 mmol) of tetrakis(triphenylphosphine)palladium(0), 1 ml (1 eq, 2.0 mmol) of 2M K$_2$CO$_3$, and 0.65 g (1 eq, 2.0 mmol) of tetrabutylammoniumbromide were put into a 100 ml round bottom flask under an argon gas atmosphere, and THF (50 ml) and toluene (20 ml) were added thereto. The reaction mixture was refluxed at 100° C. for 16 hours. When the reaction solution turned dark brown, water was added, and the resultant solution was extracted with ethylacetate. The extracted organic phase was dried over anhydrous magnesium sulfate and filtered to remove a solvent. The residue was dissolved in a trace amount of toluene and purified on a silica gel column. The resultant solid was recrystallized from toluene and methanol to give 0.98 g (56%) of a material 2 represented by Formula 11. $^1$H NMR (300 MHz, CDCl$_3$, δ): 8.11(s, 2H), 7.98(s, 2H), 7.81(s, 2H), 7.70-5.91(m, 32H), 2.51(s, 3H).

Synthesis Example 3

1) Synthesis of Intermediate B 2-bromobiphenyl (0.68 g, 2.95 mmol) was dissolved in anhydrous THF (10 ml), and the reaction mixture was cooled to −78° C. Then, t-BuLi (3.5 ml) was gradually dropwise added. The reaction mixture was stirred for one hour, and a solution of 2,6-dibromo-cyclopenta[def]phenanthrene-4-one (1 g, 2.95 mmol) in anhydrous THF (5 ml) was dropwise added thereto for 30 minutes. After the reaction was terminated, the reaction solution was concentrated under a reduced pressure and extracted with ethylacetate and brine to separate an organic phase. The organic phase was concentrated and the residue was purified by silica gel column chromatography to give an intermediate B (3.6 g).

2) Synthesis of Compound 4

The intermediate B was dissolved in acetic acid (30 ml), and the reaction mixture was cooled to 0° C. Then, a concentrated HCl (1 ml) was dropwise added, and the reaction mixture was incubated for two hours. After the reaction was terminated, the reaction solution was filtered and washed with acetic acid and methanol to give a white solid (2 g, 80%). $^1$H NMR (300 MHz, CDCl$_3$, δ): 7.22-7.26(m, 8H), 7.70(s, 2H), 7.80(s, 2H), 8.00(s, 2H)

3) Synthesis of Material 3(Formula 19)

A material 3 represented by Formula 19 was synthesized in the same manner as in Synthesis Example 1 except that the compound 4 was used instead of the compound 2, and 10-(4-tert-butyl-phenyl)-3-(4,4,5,5-tetramethyl-[1,3,2]dioxaborolane-2-yl)-10H-phenothiazine was used instead of 3-(4,4,5,5-tetramethyl-[1,3,2]dioxaborolane-2-yl)-10-p-tolyl-10H-phenoxazine. $^1$H NMR (300 MHz, CDCl$_3$, δ): 8.08(s, 2H), 7.94(s, 2H), 7.79(s, 2H), 7.75-5.88(m, 30H), 2.51(s, 3H).

Synthesis Example 4

Synthesis of Material 4(Formula 25)

A material 4 represented by Formula 25 was synthesized in the same manner as in Synthesis Example 3 except that 9-ethyl-2-(4,4,5,5-tetramethyl-[1,3,2]dioxaborolane-2-yl)-9H-carbazole was used instead of 10-(4-tert-butyl-phenyl)-3-(4,4,5,5-tetramethyl-[1,3,2]dioxaborolane-2-yl)-10H-phenothiazine. $^1$H NMR (300 MHz, CDCl$_3$, δ): 8.15(s, 2H), 7.97(s, 2H), 7.91(s, 2H), 7.77-7.21(m, 24H), 3.92(s, 2H), 1.33(s, 3H).

Evaluation Example

Evaluation of Optical Characteristics of Materials

The photoluminescence (PL) spectra of the materials 1-4 in a solution phase were measured to evaluate the emission characteristics of the materials 1-4.

Figure 2A:
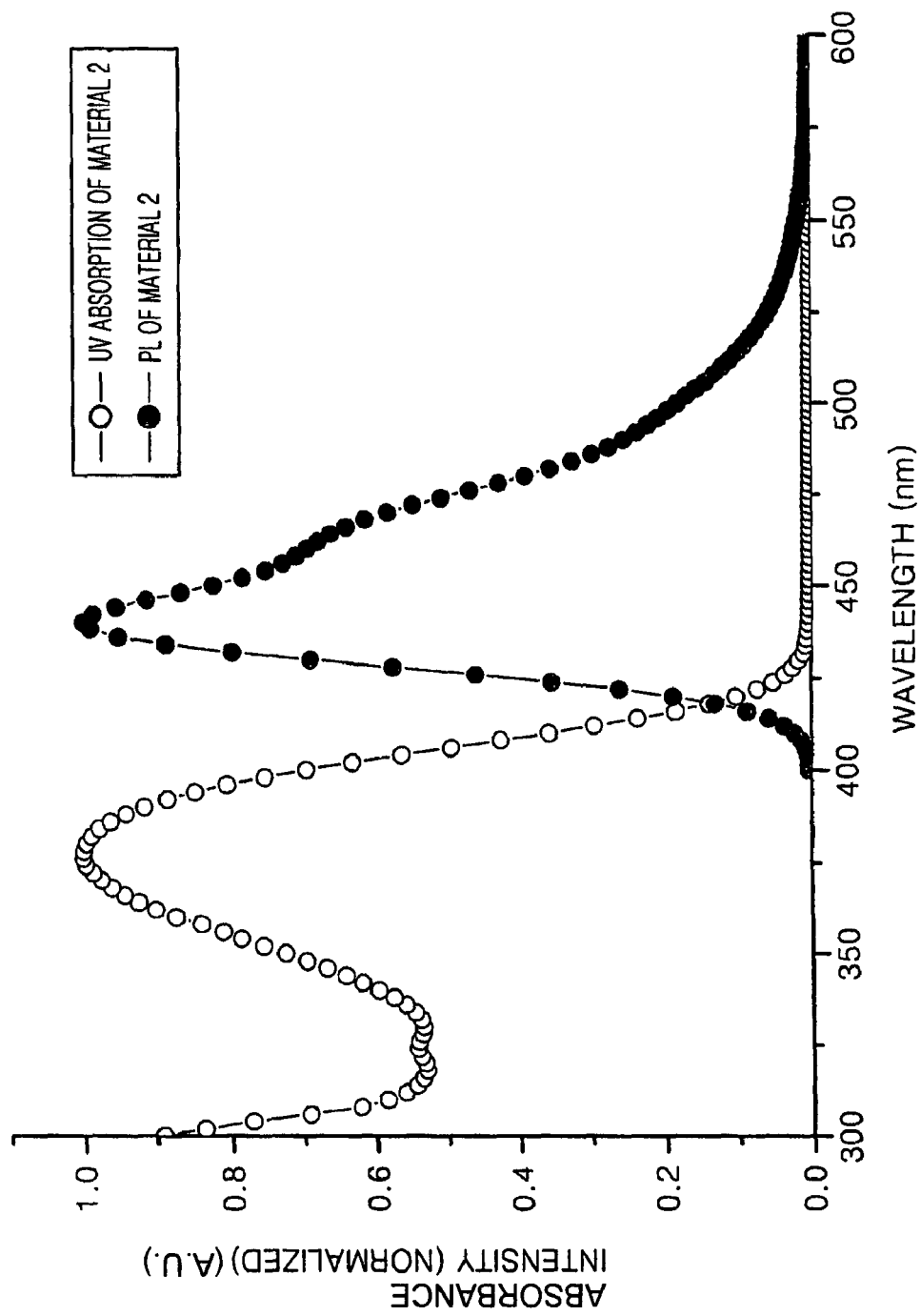
FIG. 2A shows an ultraviolet-visible spectrum and a photoluminescence spectrum of the material 2, and FIG. 2B wherein each Y is independently a substituted or unsubstituted C2-C30 alkylene group, a substituted or unsubstituted C6-C30 cycloalkylene group, a substituted or unsubstituted C6-C30 arylene group, a substituted or unsubstituted C2-C30 heteroarylene group, or a substituted or unsubstituted C2-C30 alkenylene group.

In order to evaluate optical characteristics of a solution phase, each of the materials 1-4 was diluted with toluene to a concentration of 10 mM, and the PL spectra of the diluted solutions were measured using an ISC PC1 spectrofluorometer equipped with a xenon lamp. Also, the UV absorption spectra of the diluted solutions were measured using a Shimadzu UV-350 Spectrometer. The UV and PL results of the materials 1-4 are presented in Table 1 below. As shown in Table 1, it can be seen that the materials 1-4 according to the present invention had emission characteristics suitable for organoelectroluminescent devices. The ultraviolet-visible spectrum and the photoluminescence spectrum of the material 2 are shown in FIG. 2A.

TABLE 1

| Material | UV($\lambda_{max}$)(nm) | PL($\lambda_{max}$)(nm) |
|---|---|---|
| 1 | 378 | 436 |
| 2 | 377 | 440 |
| 3 | 376 | 461 |
| 4 | 328 | 414 |

Example 1

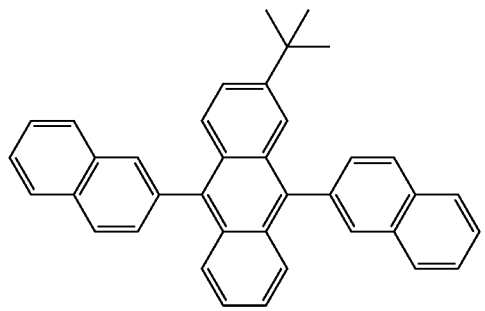

<Formula 29>

Organoelectroluminescent devices having the following structure were manufactured using the material 1 as a dopant of an emitting layer and a compound of Formula 29 above as a host of the emitting layer: ITO/PEDOT (400 Å)/Formula 29 material 1 (300 Å)/Alq3(40 Å)/Li F(10 Å)/Al(2000 Å).

A 15 Ω/cm$^2$ (1,000 Å) ITO glass substrate was cut into pieces of 50 mm×50 mm×0.7 mm in size, followed by ultrasonic cleaning in acetone, isopropyl alcohol, and pure water (15 minutes for each) and then UV/ozone cleaning (30 minutes) to form anodes. PEDOT-PSS (AI4083) (Bayer) was coated on the anodes and heated at 110° C. for five minutes in the atmosphere and then at 200° C. for five minutes under a nitrogen atmosphere to form hole injection layers with a thickness of 400 Å. A mixture of 0.1 g of the host and 0.01 g of the dopant (10 parts by weight of the material 1 based on 100 parts by weight of the compound of Formula 29) were spin-coated on the hole injection layers and heated at 10° C. for 30 minutes to form emitting layers with a thickness of 300 Å. Then, an Alq3 compound was vacuum-deposited to a thickness of 40 Å on the emitting layers to form electron transport layers. LiF (10 Å, electron injection layers) and Al (2000 Å, cathodes) were sequentially vacuum-deposited on the electron transport layers to thereby complete organoelectroluminescent devices as illustrated in FIG. 1A. The organoelectroluminescent devices exhibited blue emission of 1,500 cd/m$^2$ at a voltage of 8 V and efficiency of 1.1 cd/A.

Example 2

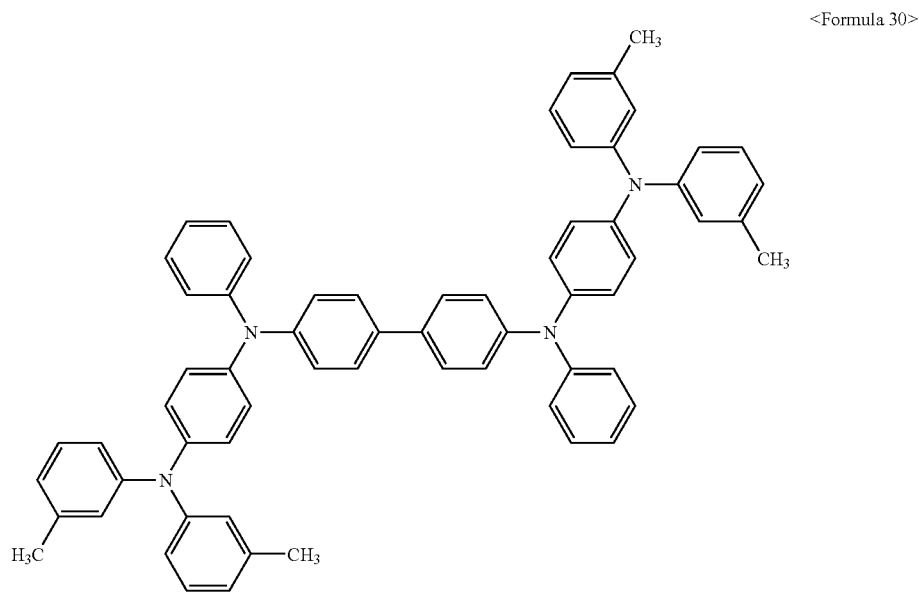
<Formula 30>

Organoelectroluminescent devices having the following structure were manufactured using the material 2 as a dopant of an emitting layer and the compound of Formula 29 above as a host of the emitting layer: ITO/Formula 30 (200 Å)/α-NPD(300 Å)/Formula 29: material 2 (300 Å)/Alq3(40 Å)/LiF (10 Å)/Al(2000 Å).

A 15 Ω/cm$^2$ (1,000 Å) ITO glass substrate was cut into pieces of 50 mm×50 mm×0.7 mm in size, followed by ultrasonic cleaning in acetone, isopropyl alcohol, and pure water (15 minutes for each) and then UV/ozone cleaning (30 minutes) to form anodes. The compound of Formula 30 (hole injection layers) and α-NPD (hole transport layers) were vacuum-deposited on the anodes, and a mixture of the compound of Formula 29 and the material 2 (weight ratio of 100:10) was then vacuum-deposited to form emitting layers. Then, an Alq3 compound was vacuum-deposited to a thickness of 40 Å on the emitting layers to form electron transport layers. LiF (10 Å, electron injection layers) and Al (2000 Å, cathodes) were sequentially vacuum-deposited on the electron transport layers to thereby complete organoelectroluminescent devices as illustrated in FIG. 1B. The organoelectroluminescent devices exhibited blue emission of 7,100 cd/m$^2$ at a voltage of 10 V and efficiency of 4.15 cd/A.

Example 3

Organoelectroluminescent devices having the following structure were manufactured in the same manner as in Example 2 except that the compound of Formula 29 was used as a host of an emitting layer and the material 3 was used as a dopant of the emitting layer: ITO/Formula 30 (200 Å)/α-NPD(300 Å)/Formula 29 material 3 (300 Å)/Alq3(40 Å)/LiF (10 Å)/Al(2000 Å). The organoelectroluminescent devices exhibited blue emission of 8,500 cd/m$^2$ at a voltage of 10 V and efficiency of 3.6 cd/A.

Example 4

Organoelectroluminescent devices having the following structure were manufactured in the same manner as in Example 2 except that the compound of Formula 29 was used as a host of an emitting layer and the material 4 was used as a dopant of the emitting layer: ITO/Formula 30 (200 Å)/α-NPD(300 Å)/Formula 29: material 4 (300 Å)/Alq3(40 Å)/LiF (10 Å)/Al(2000 Å). The organoelectroluminescent devices exhibited blue emission of 2,500 cd/m$^2$ at a voltage of 10V and efficiency of 1.8 cd/A.

Figure 2B:
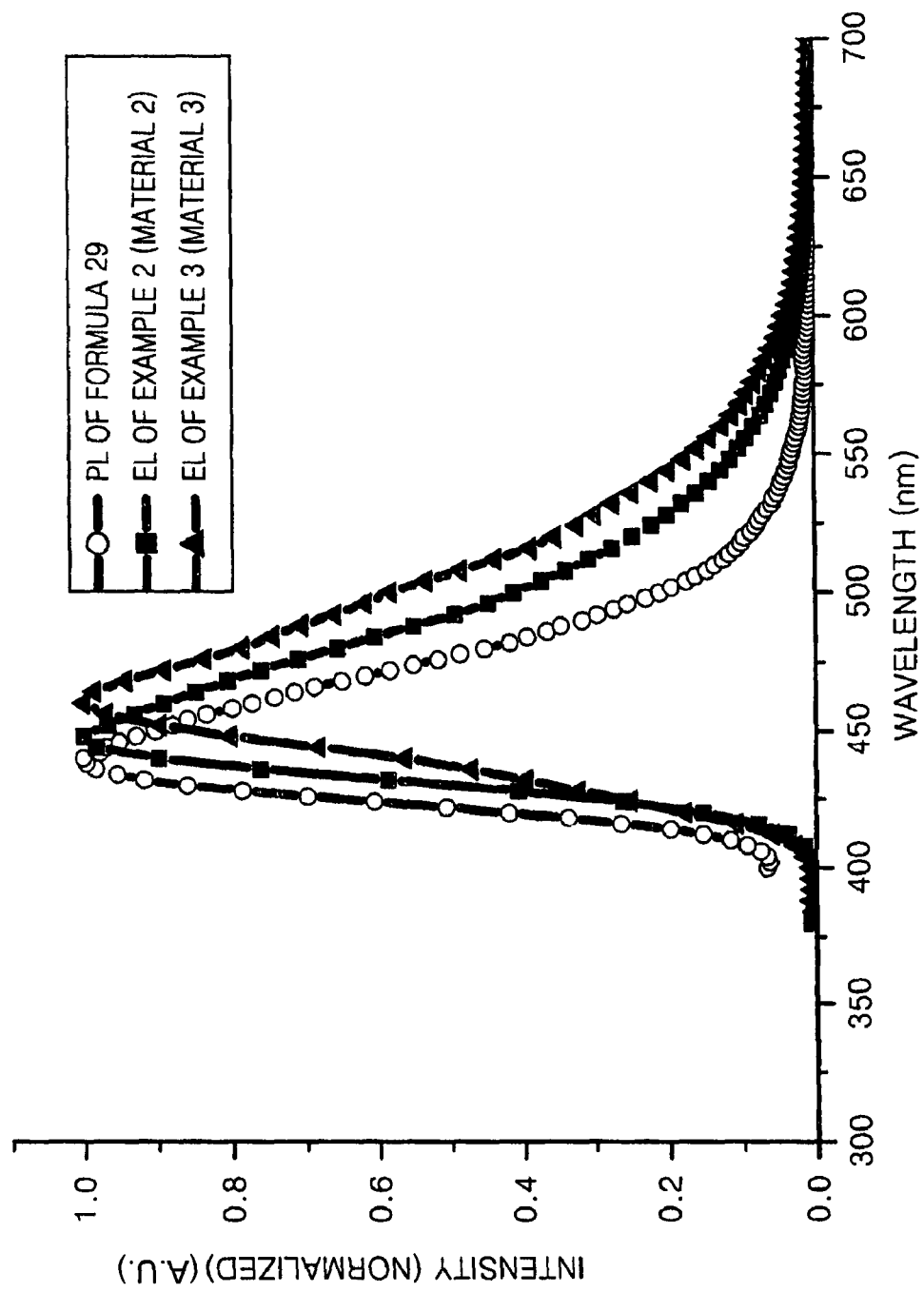

The photoluminescence spectrum of the compound of Formula 29 and the electroluminescence spectrum of Examples 2 and 3 are shown in FIG. 2B.

The above Examples show that materials according to the present invention have good EL characteristics as phosphorescent and fluorescent materials.

A compound of Formula 1 according to the present invention is adapted for both dry and wet processes, and has good emission characteristics and thermal stability. Therefore, the use of the compound of the present invention enables to produce an organoelectroluminescent device having a low driving voltage and good color purity and efficiency.

Other embodiments of the invention, including modifications and adaptions of the disclosed embodiments, will be apparent to those skilled in the art from consideration of the specification and practice of the invention disclosed herein. The foregoing descriptions of implementations of the invention have been presented for purposes of illustration and description. The descriptions are not exhaustive and do not limit the invention to the precise form disclosed. Modifications and variations are possible in light of the above teachings or may be acquired from practicing the invention.

What is claimed is:

1. A cyclopentaphenanthrene-based compound represented by Formula 1 below:

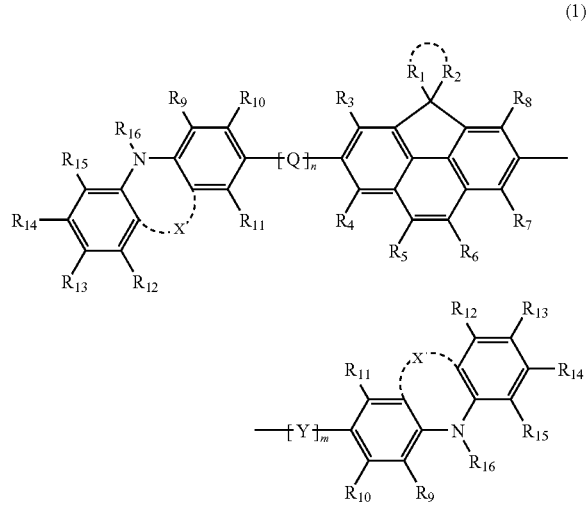

(1)

wherein each Y is independently a substituted or unsubstituted C2-C30 alkylene group, a substituted or unsubstituted C6-C30 cycloalkylene group, a substituted or unsubstituted C6-C30 arylene group, a substituted or unsubstituted C2-C30 heteroarylene group, or a substituted or unsubstituted C2-C30 alkenylene group;

each Q is independently a substituted or unsubstituted C2-C30 alkylene group, a substituted or unsubstituted C6-C30 cycloalkylene group, a substituted or unsubstituted C6-C30 arylene group, a substituted or unsubstituted C2-C30 heteroarylene group, or a substituted or unsubstituted C2-C30 alkenylene group;

m is an integer of 0 to 5, and when m is an integer of 2 or more, Ys are the same or different from each other;

n is an integer of 0 to 5, and when n is an integer of 2 or more, Qs are the same or different from each other;

$R_1$ and $R_2$ are each independently hydrogen, halogen, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 aralkyl group, or a substituted or unsubstituted C2-C30 heteroaryl group, and $R_1$ and $R_2$ can be optionally linked together to form a substituted or unsubstituted C3-C20 aliphatic ring, a substituted or unsubstituted C5-C30 heteroaliphatic ring, a substituted or unsubstituted C6-C30 aromatic ring, or a substituted or unsubstituted C2-C30 heteroaromatic ring, with the proviso that, when m and n are 1, X is O , and $R_{16}$ is a substituted C6-C30 aryl group, $R_1$ and $R_7$ are each independently hydrogen, halogen, a cyano group, a hydroxyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 aralkyl group, or a substituted or unsubstituted C2-C30 heteroaryl group, and $R_1$ and $R_2$ can be optionally linked together to form a substituted or unsubstituted C3-C20 aliphatic ring, a substituted or unsubstituted C5-C30 heteroaliphatic ring, a substituted or unsubstituted C6-C30 aromatic ring, or a substituted or unsubstituted C2-C30 heteroaromatic ring;

$R_3$ through $R_{16}$ are each independently hydrogen, halogen, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 aralkyl group, or a substituted or unsubstituted C2-C30 heteroaryl group; and X is a single bond, —CH=CH—, —O—, —S—, —Se—, —(CH$_2$)$_q$— where q is an integer of 1 to 5, or —C(R') (R")— where R' and R" are each independently hydrogen, halogen, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 aralkyl group, or a substituted or unsubstituted C2-C30 heteroaryl group.

2. The cyclopentaphenanthrene-based compound of claim 1, wherein the

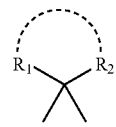

in Formula 1 is represented by one of Formulae 2 through 5:

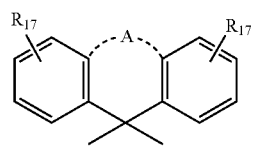

(2)

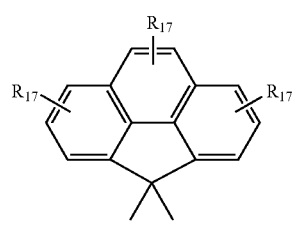

(3)

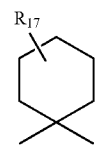

(4)

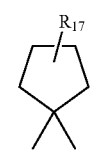

(5)

wherein each $R_{17}$ is independently hydrogen, halogen, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 aralkyl group, a substituted or unsubstituted C2-C30 heteroaryl group, —N($Z_1$)($Z_2$) or —Si($Z_3$)($Z_4$)($Z_5$) where $Z_1$, $Z_2$, $Z_3$, $Z_4$, and $Z_5$ are each independently hydrogen, a substituted or unsubstituted C1-C20 alkyl group, a substituted or unsubstituted C6-C30 aryl group, a substituted or unsubstituted C2-C30 heteroaryl group, a substituted or unsubstituted C5-C20 cycloalkyl group, or a substituted or unsubstituted C5-C30 heterocycloalkyl group; and A is a single bond, —O—, —S—, —Se—, or —$(CH_2)_p$— where p is an integer of 1 to 5.

3. The cyclopentaphenanthrene-based compound of claim 1, which is a compound selected from the group consisting of compounds represented by Formulae 6 through 8 below:

each Q is independently a substituted or unsubstituted C2-C30 alkylene group, a substituted or unsubstituted C6-C30 cycloalkylene group, a substituted or unsubstituted C6-C30 arylene group, a substituted or unsubstituted C2-C30 heteroarylene group, or a substituted or unsubstituted C2-C30 alkenylene group;

m is an integer of 0 to 5, and when m is an integer of 2 or more, Ys may be the same or different from each other;

n is an integer of 0 to 5, and when n is an integer of 2 or more, Qs may be the same or different from each other;

$R_9$ through $R_{16}$ are each independently hydrogen, halogen, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or

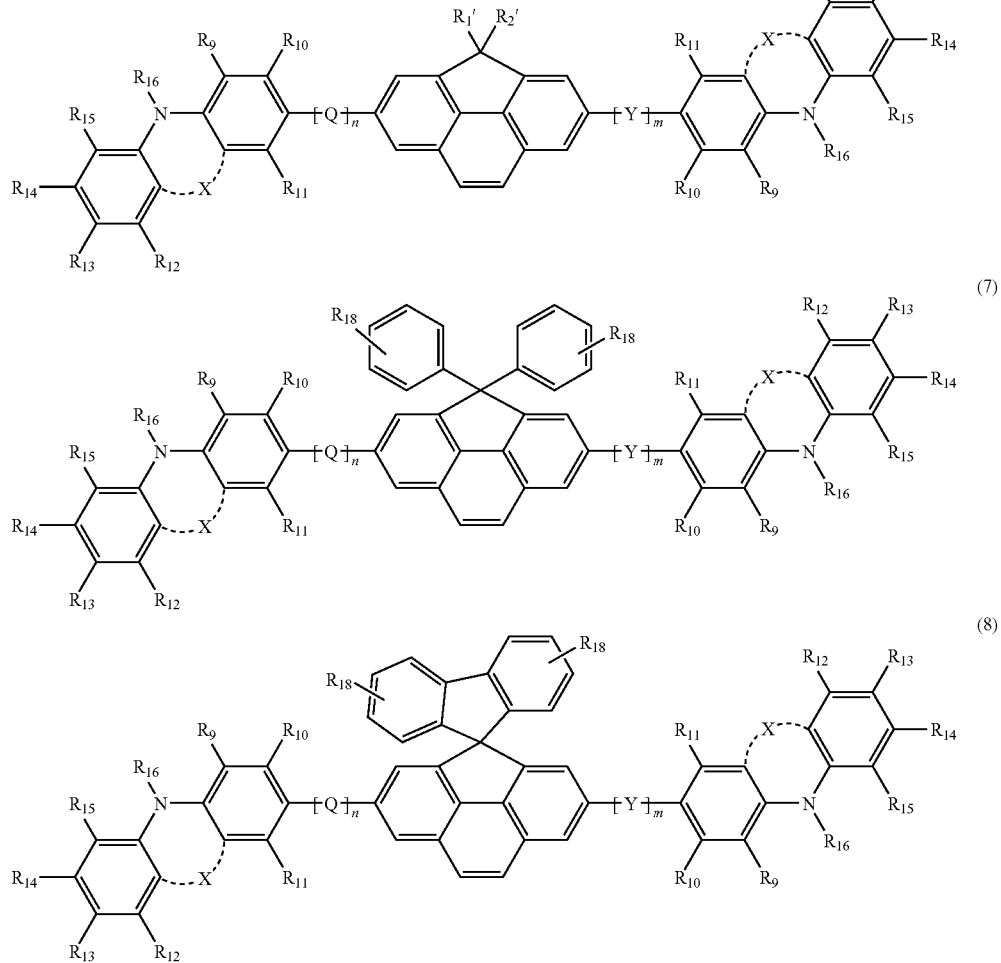

wherein each Y is independently a substituted or unsubstituted C2-C30 alkylene group, a substituted or unsubstituted C6-C30 cycloalkylene group, a substituted or unsubstituted C6-C30 arylene group, a substituted or unsubstituted C2-C30 heteroarylene group, or a substituted or unsubstituted C2-C30 alkenylene group;

unsubstituted C6-C30 aralkyl group, or a substituted or unsubstituted C2-C30 heteroaryl group;

X is a single bond, —CH═CH—, —O—, —S—, —Se—, —$(CH_2)_q$— where q is an integer of 1 to 5, or —C(R')(R")— where R' and R" are each independently hydrogen, halogen, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 aralkyl group, or a substituted or unsubstituted C2-C30 heteroaryl group;

$R_1'$ and $R_2'$ are each independently hydrogen, halogen, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 aralkyl group, or a substituted or unsubstituted C2-C30 heteroaryl group, with the proviso that, when m and n are 1, X is O, and $R_{16}$ is a substituted C6-C30 aryl group, $R_1'$ and $R_2'$ are each independently hydrogen, halogen, a cyano group, a hydroxyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 aralkyl group, or a substituted or unsubstituted C2-C30 heteroaryl group; and each $R_{18}$ is independently hydrogen, halogen, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 aralkyl group, a substituted or unsubstituted C2-C30 heteroaryl group, $-N(Z_1)(Z_2)$ or $-Si(Z_3)(Z_4)(Z_5)$ where $Z_1, Z_2, Z_3, Z_4$, and $Z_5$ are each independently hydrogen, a substituted or unsubstituted C1-C20 alkyl group, a substituted or unsubstituted C6-C30 aryl group, a substituted or unsubstituted C2-C30 heteroaryl group, a substituted or unsubstituted C5-C20 cycloalkyl group, or a substituted or unsubstituted C5-C30 heterocycloalkyl group.

4. The cyclopentaphenanthrene-based compound of claim 1, which is a compound selected from compounds represented by Formulae 11 through 28 below:

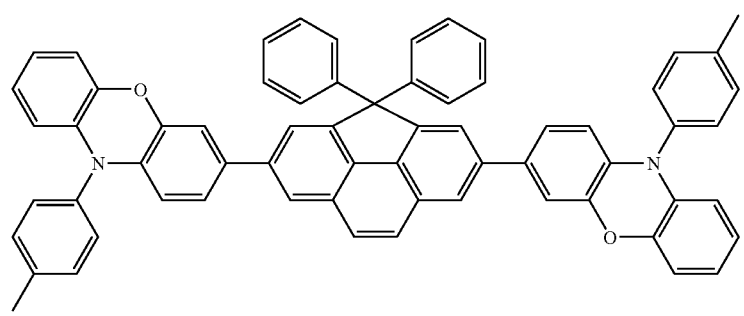

(11)

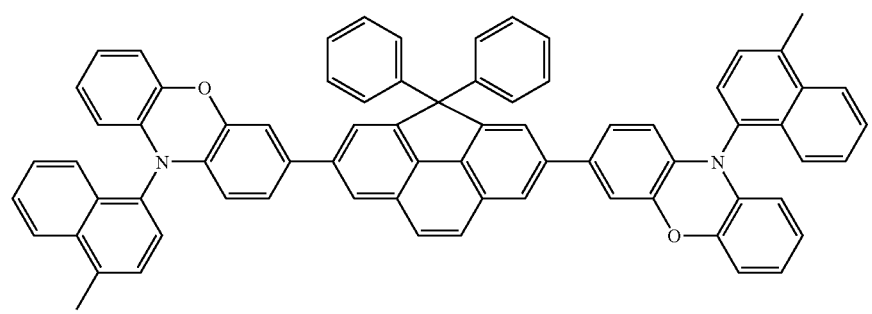

(12)

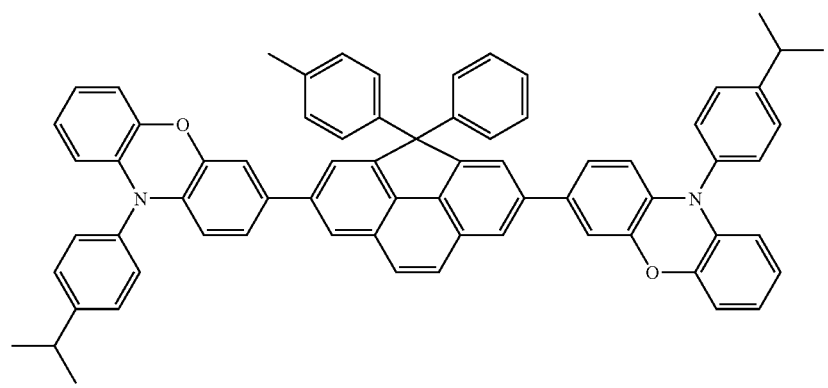

(13)

-continued
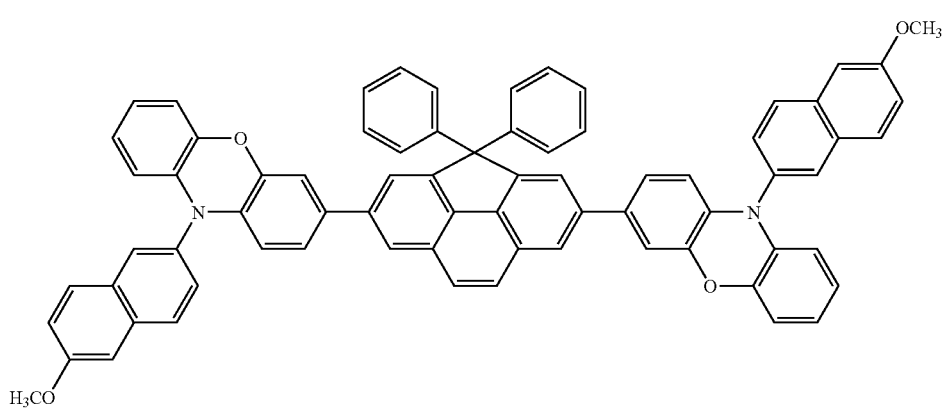
(14)
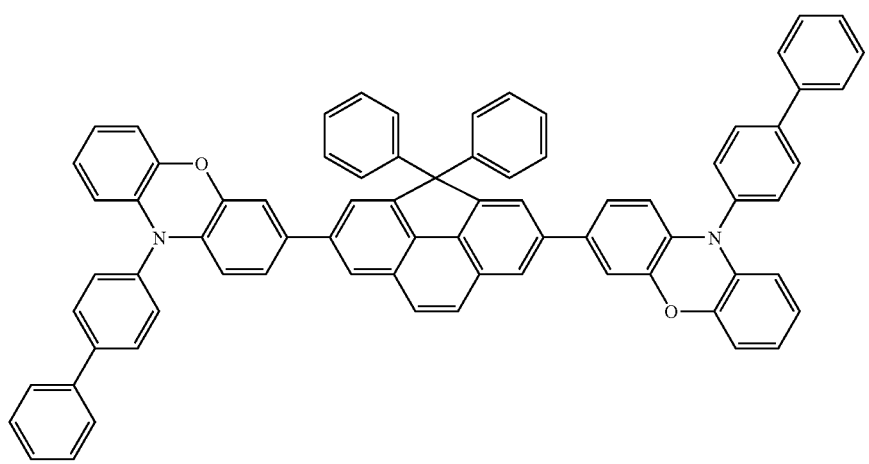
(15)
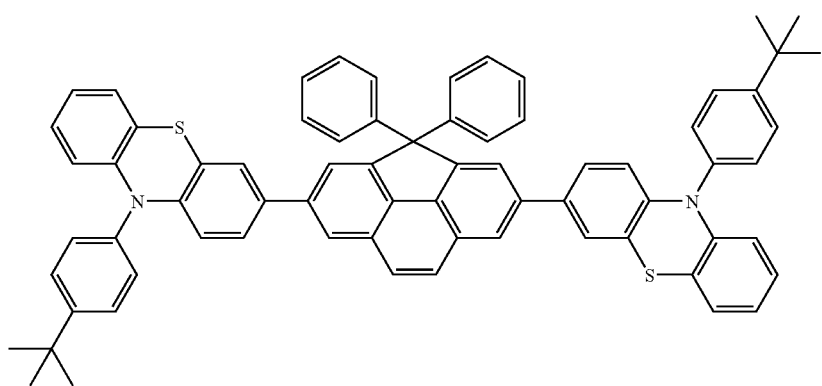
(16)
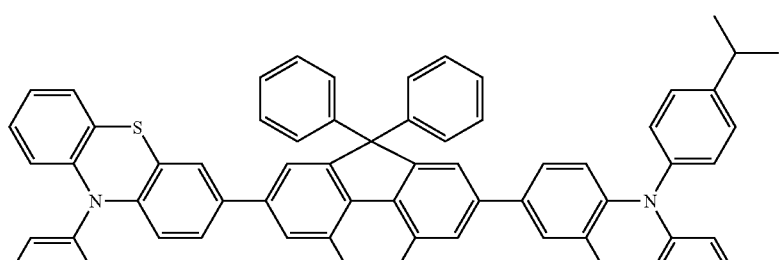
(17)

5. An organoelectroluminescent device comprising a pair of electrodes and at least one organic layer interposed between the pair of electrodes, said at least one organic layer comprising an organic layer formed of the compound of claim 1, said organic layer formed of the compound of claim 1 comprising at least one of an emitting layer, a hole injection layer, and a hole transport layer.

6. An organoelectroluminescent device comprising:
a first electrode;
a second electrode; and
at least one organic layer interposed between the first electrode and the second electrode, the organic layer comprising a cyclopentaphenanthrene-based compound represented by Formula 1 below:

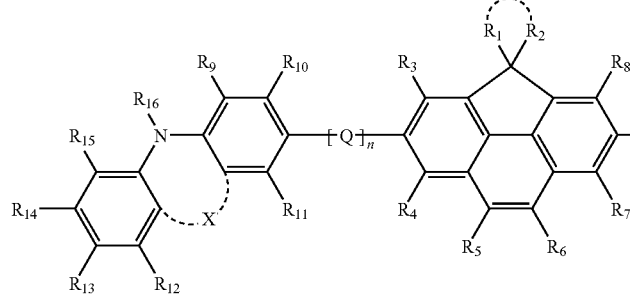
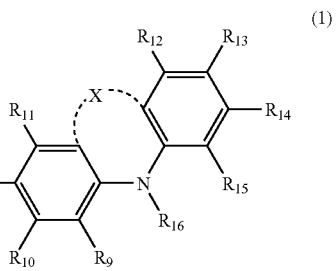

(1)

wherein each Y is independently a substituted or unsubstituted C2-C30 alkylene group, a substituted or unsubstituted C6-C30 cycloalkylene group, a substituted or unsubstituted C6-C30 arylene group, a substituted or unsubstituted C2-C30 heteroarylene group, or a substituted or unsubstituted C2-C30 alkenylene group;

each Q is independently a substituted or unsubstituted C2-C30 alkylene group, a substituted or unsubstituted C6-C30 cycloalkylene group, a substituted or unsubstituted C6-C30 arylene group, a substituted or unsubstituted C2-C30 heteroarylene group, or a substituted or unsubstituted C2-C30 alkenylene group;

m is an integer of 0 to 5, and when m is an integer of 2 or more, Ys are the same or different from each other;

n is an integer of 0 to 5, and when n is an integer of 2 or more, Qs are the same or different from each other;

$R_1$ and $R_2$ are each independently hydrogen, halogen, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 aralkyl group, or a substituted or unsubstituted C2-C30 heteroaryl group, and $R_1$ and $R_2$ can be optionally linked together to form a substituted or unsubstituted C3-C20 aliphatic ring, a substituted or unsubstituted C5-C30 heteroaliphatic ring, a substituted or unsubstituted C6-C30 aromatic ring, or a substituted or unsubstituted C2-C30 heteroaromatic ring, with the proviso that, when m and n are 1, X is O, and $R_{16}$ is a substituted C6-C30 aryl group, $R_1$ and $R_2$ are each independently hydrogen, halogen, a cyano group, a hydroxyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 aralkyl group, or a substituted or unsubstituted C2-C30 heteroaryl group, and $R_1$ and $R_2$ can be optionally linked together to form a substituted or unsubstituted C3-C20 aliphatic ring, a substituted or unsubstituted C5-C30 heteroaliphatic ring, a substituted or unsubstituted C6-C30 aromatic ring, or a substituted or unsubstituted C2-C30 heteroaromatic ring;

$R_3$ through $R_{16}$ are each independently hydrogen, halogen, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 aralkyl group, or a substituted or unsubstituted C2-C30 heteroaryl group; and X is a single bond, —CH═CH—, —O—, —S—, —Se—, —(CH$_2$)$_q$— where q is an integer of 1 to 5, or —C(R')(R")— where R' and R" are each independently hydrogen, halogen, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 aralkyl group, or a substituted or unsubstituted C2-C30 heteroaryl group.

7. The organoelectroluminescent device of claim 6, wherein the organic layer is an emitting layer, a hole injection layer, or a hole transport layer.

8. The organoelectroluminescent device of claim 6, further comprising at least one selected from the group consisting of a hole injection layer, a hole transport layer, an electron blocking layer, a hole blocking layer, an electron transport layer, and an electron injection layer, between the first electrode and the second electrode.

9. The organoelectroluminescent device of claim 6, wherein the cyclopentaphenanthrene-based compound is represented by one selected from the group consisting of Formulae 6 through 8:

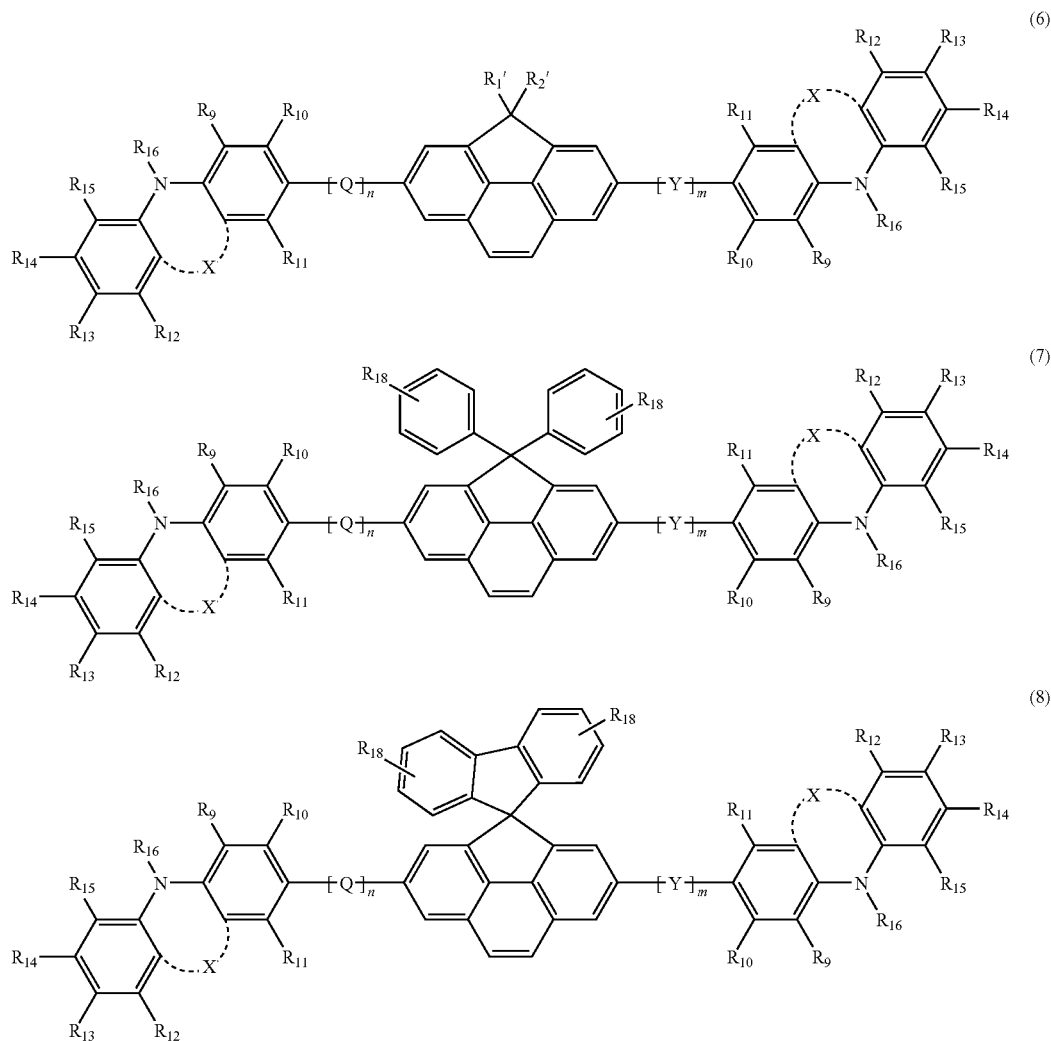

wherein each Y is independently a substituted or unsubstituted C2-C30 alkylene group, a substituted or unsubstituted C6-C30 cycloalkylene group, a substituted or unsubstituted C6-C30 arylene group, a substituted or unsubstituted C2-C30 heteroarylene group, or a substituted or unsubstituted C2-C30 alkenylene group;

each Q is independently a substituted or unsubstituted C2-C30 alkylene group, a substituted or unsubstituted C6-C30 cycloalkylene group, a substituted or unsubstituted C6-C30 arylene group, a substituted or unsubstituted C2-C30 heteroarylene group, or a substituted or unsubstituted C2-C30 alkenylene group;

m is an integer of 0 to 5, and when m is an integer of 2 or more, Ys may be the same or different from each other;

n is an integer of 0 to 5, and when n is an integer of 2 or more, Qs may be the same or different from each other;

$R_9$ through $R_{16}$ are each independently hydrogen, halogen, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 aralkyl group, or a substituted or unsubstituted C2-C30 heteroaryl group;

X is a single bond, —CH=CH—, —O—, —S—, —Se—, —(CH$_2$)$_q$— where q is an integer of 1 to 5, or —C(R')(R")— where R' and R" are each independently hydrogen, halogen, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 aralkyl group, or a substituted or unsubstituted C2-C30 heteroaryl group;

$R_1'$ and $R_2'$ are each independently hydrogen, halogen, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 aralkyl group, or a substituted or unsubstituted C2-C30 heteroaryl group, and $R_1$ and $R_2$ can be optionally linked together to form a substituted or unsubstituted C3-C20 aliphatic ring, a substituted or unsubstituted C5-C30 heteroaliphatic ring, a substituted or unsubstituted C6-C30 aromatic ring, or a substituted or unsubstituted C2-C30 heteroaromatic ring; and each $R_{18}$ is independently hydrogen, halogen, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 aralkyl group, a substituted or unsubstituted C2-C30 heteroaryl group, $-N(Z_1)(Z_2)$ or $-Si(Z_3)(Z_4)(Z_5)$ where $Z_1$, $Z_2$, $Z_3$, $Z_4$, and $Z_5$ are each independently hydrogen, a substituted or unsubstituted C1-C20 alkyl group, a substituted or unsubstituted C6-C30 aryl group, a substituted or unsubstituted C2-C30 heteroaryl group, a substituted or unsubstituted C5-C20 cycloalkyl group, or a substituted or unsubstituted C5-C30 heterocycloalkyl group.

10. The organoelectroluminescent device of claim 6, wherein the cyclopentaphenanthrene-based compound is represented by one selected from the group consisting of Formulae 11 through 28:

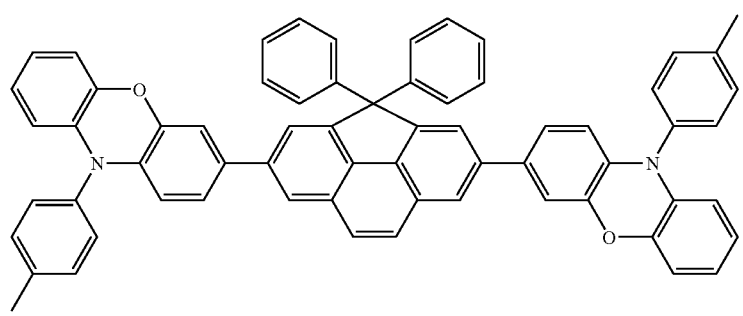

(11)

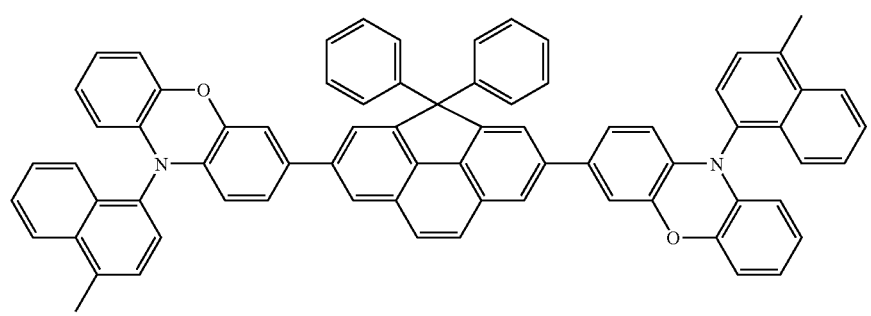

(12)

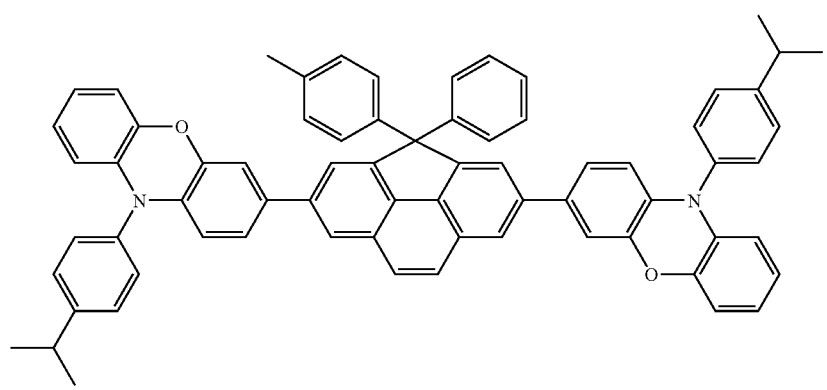

(13)

-continued
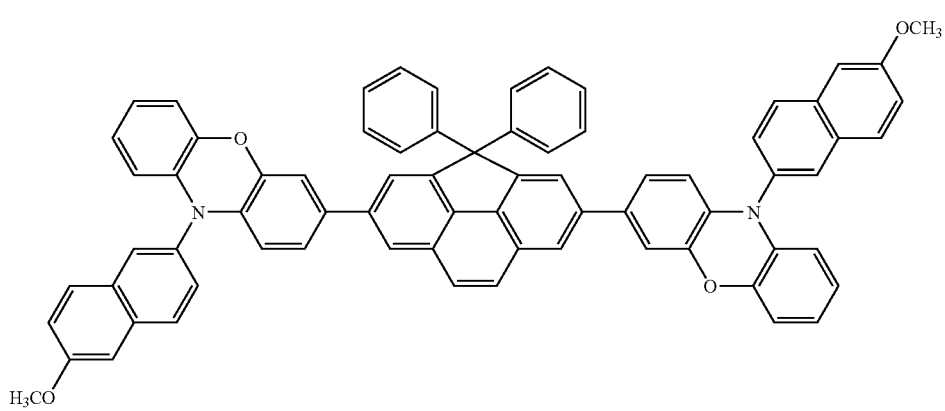
(14)
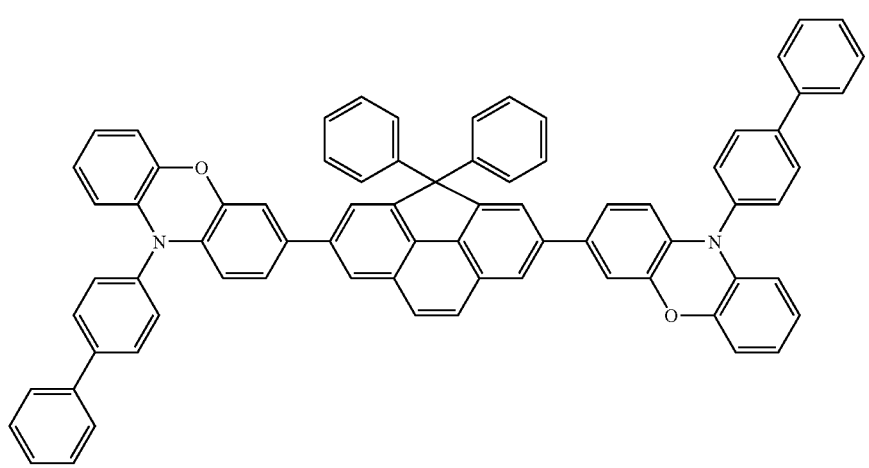
(15)
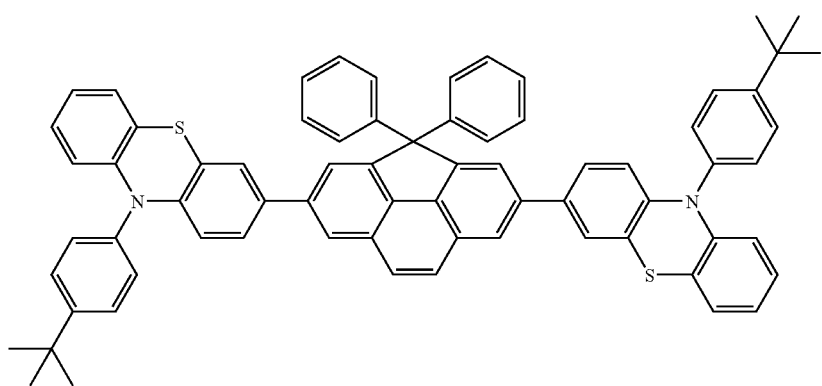
(16)
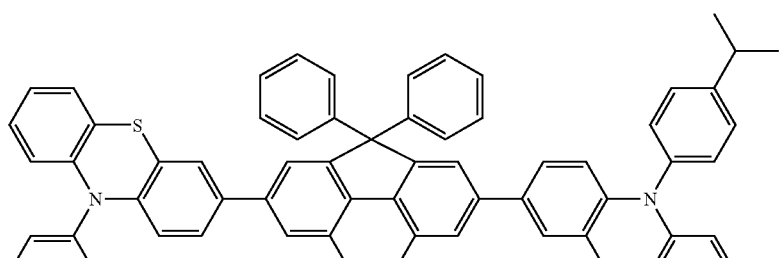
(17)

11. The organoelectroluminescent device of claim 6, wherein said at least one organic layer comprises a hole injection layer comprised of the cyclopentaphenanthrene-based compound.

12. The organoelectroluminescent device of claim 6, wherein said at least one organic layer comprises a hole transport layer comprised of the cyclopentaphenanthrene-based compound.

13. The organoelectroluminescent device of claim 6, wherein said at least one organic layer comprises an emitting layer comprised of the cyclopentaphenanthrene-based compound.

14. The organoelectroluminescent device of claim 13, wherein the emitting layer further comprises a fluorescent host material.

15. The organoelectroluminescent device of claim 13, wherein the emitting layer further comprises a dopant material.

16. The organoelectroluminescent device of claim 13, wherein the cyclopentaphenanthrene-based compound is used as a phosphorescent host material.

17. The organoelectroluminescent device of claim 16, wherein the emitting layer further comprises at least one of 4,4'-N,N'-dicarbazole-biphenyl (CBP) and poly(n-vinylcarbazole) (PVK).

18. The organoelectroluminescent device of claim 13, wherein the emitting layer comprises a host material represented by Formula 29 and a dopant of the cyclopentaphenanthrene-based compound:

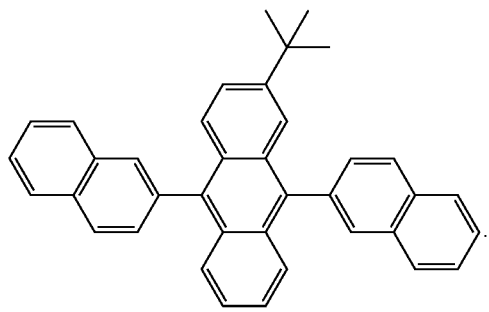

(29)

19. An organoelectroluminescent device comprising:

a first electrode;

a second electrode facing the first electrode; and at least one organic layer interposed between the first electrode and the second electrode, the organic layer comprising a cyclopentaphenanthrene-based compound represented by one of Formulae 6 to 9:

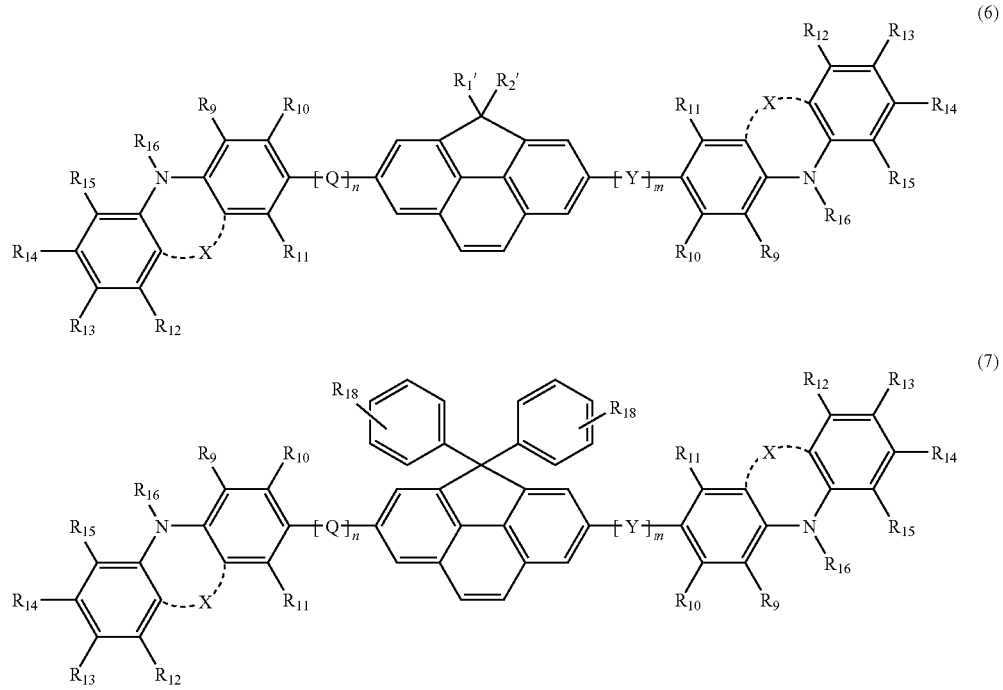

-continued (8)

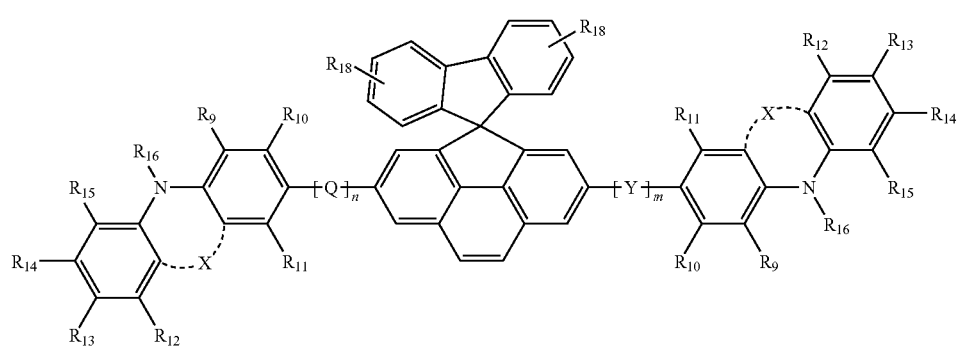

wherein each Y is independently a substituted or unsubstituted C2-C30 alkylene group, a substituted or unsubstituted C6-C30 cycloalkylene group, a substituted or unsubstituted C6-C30 arylene group, a substituted or unsubstituted C2-C30 heteroarylene group, or a substituted or unsubstituted C2-C30 alkenylene group;

each Q is independently a substituted or unsubstituted C2-C30 alkylene group, a substituted or unsubstituted C6-C30 cycloalkylene group, a substituted or unsubstituted C6-C30 arylene group, a substituted or unsubstituted C2-C30 heteroarylene group, or a substituted or unsubstituted C2-C30 alkenylene group;

m is an integer of 0 to 5, and when m is an integer of 2 or more, Ys may be the same or different from each other;

n is an integer of 0 to 5, and when n is an integer of 2 or more, Qs may be the same or different from each other;

$R_9$ through $R_{16}$ are each independently hydrogen, halogen, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 aralkyl group, or a substituted or unsubstituted C2-C30 heteroaryl group;

X is a single bond, —CH=CH—, —O—, —S—, —Se—, —$(CH_2)_q$— where q is an integer of 1 to 5, or —C(R')(R")— where R' and R" are each independently hydrogen, halogen, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 aralkyl group, or a substituted or unsubstituted C2-C 30 heteroaryl group;

$R_1$' and $R_2$' are each independently hydrogen, halogen, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 aralkyl group, or a substituted or unsubstituted C2-C30 heteroaryl group, with the proviso that when m and n are 1, X is O, and $R_{16}$ is a substituted C6-C30 aryl group, and $R_1$' and $R_2$' are each independently hydrogen, halogen, a cyano group, a hydroxyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 aralkyl group, or a substituted or unsubstituted C2-C30 heteroaryl group; and each $R_{18}$ is independently hydrogen, halogen, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 aralkyl group, a substituted or unsubstituted C2-C30 heteroaryl group, —$N(Z_1)(Z_2)$ or —$Si(Z_3)(Z_4)(Z_5)$ where $Z_1$, $Z_2$, $Z_3$, $Z_4$, and $Z_5$ are each independently hydrogen, a substituted or unsubstituted C1-C20 alkyl group, a substituted or unsubstituted C6-C30 aryl group, a substituted or unsubstituted C2-C30 heteroaryl group, a substituted or unsubstituted C5-C20 cycloalkyl group, or a substituted or unsubstituted C5-C30 heterocycloalkyl group.

20. The organoelectroluminescent device of claim 19, wherein said at least one organic layer comprises at least one of an emitting layer comprised of the cyclopentaphenanthrene-based compound, a hole injection layer comprised of the cyclopentaphenanthrene-based compound and a hole transport layer comprised of the cyclopentaphenanthrene-based compound.

* * * * *